(12) United States Patent
Fu et al.

(10) Patent No.: US 7,022,694 B2
(45) Date of Patent: Apr. 4, 2006

(54) INDOLES AND INDOLINES HAVING 5-HT ACTIVITY

(75) Inventors: Jian-Min Fu, Kalamazoo, MI (US); Jeanette Kay Morris, Kalamazoo, MI (US); Arthur Glenn Romero, Kalamazoo, MI (US)

(73) Assignee: Pharmacia & UpJohn Company, Kalamazoo, MI (US)

( * ) Notice: Subject to any disclaimer, the term of this patent is extended or adjusted under 35 U.S.C. 154(b) by 322 days.

(21) Appl. No.: 10/192,918

(22) Filed: Jul. 11, 2002

(65) Prior Publication Data

US 2003/0060458 A1 Mar. 27, 2003

Related U.S. Application Data

(60) Provisional application No. 60/305,305, filed on Jul. 13, 2001.

(51) Int. Cl.
*A61P 25/00* (2006.01)
*A61K 31/55* (2006.01)
*C07D 487/00* (2006.01)

(52) U.S. Cl. ..................... 514/215; 540/580
(58) Field of Classification Search ................ 514/215; 540/580
See application file for complete search history.

(56) References Cited

FOREIGN PATENT DOCUMENTS

| WO | 94/20472 | 9/1994 |
|---|---|---|
| WO | 96/08494 | 3/1996 |
| WO | 98/14447 | 4/1998 |
| WO | 98/40385 | 9/1998 |
| WO | 99/49864 | 10/1999 |
| WO | WO 01/12602 | 2/2001 |

OTHER PUBLICATIONS

"6, 7, 8, 9-Tetrahydro-N,N-DI-N-Propyl-3H-Benzindol-8-Amines Derivatives as Potent and Orally Active Serotonin 5-HRT1A Receptor Agonists", Journal of Medicinal Chemistry, American Chemical Society, vol. 37, 1994, pp. 3263-3273 (6 sheets).

"Photochemical Synthesis of Azepinoindoles and Azocinoindoles From N-Chloro-Acetylindolylethylamines, and a Mechanistic Study Based on the Correlation Between Quantum Yields and Calculated Frontier Electron Densities of Indole Radicals", Chemical and Pharmaceutical Bulletin, Pharmaceutical Society of Japan, vol. 28, No. 3, 1980, pp. 900-909 (5 sheets).

*Primary Examiner*—Brenda Coleman
(74) *Attorney, Agent, or Firm*—Mehdi Ganjeizadeh; Charles W. Ashbrook

(57) ABSTRACT

The present invention provides compounds of Formula (I):

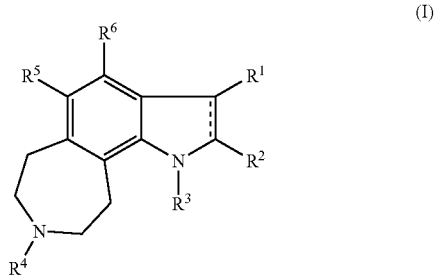

(I)

wherein $R^1$, $R^2$, $R^3$, $R^4$, $R^5$, $R^6$ and --- have any of the values defined in the specification, as well as pharmaceutical compositions comprising the compounds. The invention also provides therapeutic methods as well as processes and intermediates useful for preparing compounds of Formula (I). The compounds are useful as 5-HT ligands.

34 Claims, No Drawings

INDOLES AND INDOLINES HAVING 5-HT ACTIVITY

CROSS-REFERENCE TO RELATED APPLICATIONS

This application claims the benefit of U.S. provisional application Ser. No. 60/305305 filed on Jul. 13, 2001, under 35 USC 119(e)(i).

FIELD OF THE INVENTION

The present invention provides tricyclic hexahydroazepinoindole and indoline derivatives, and more specifically, provides compounds of Formula (I) described herein below. These compounds are 5-HT ligands, and are useful for treating diseases wherein modulation of 5-HT activity is desired.

BACKGROUND OF THE INVENTION

Serotonin has been implicated in a number of diseases and conditions that originate in the central nervous system. These include diseases and conditions related to sleeping, eating, perceiving pain, controlling body temperature, controlling blood pressure, depression, anxiety, schizophrenia, and other bodily states. (R. W. Fuller, Biology of Serotonergic Transmission, ed. Neville V. Osborne, John Wiley and Sons (1982), p 221; D. J. Boullin, Serotonin in Mental Abnormalities 1, John Wiley and Sons (1978), p. 316; J. Barchas, et al., Serotonin and Behavior, Academic Press, New York, N.Y. (1973).) Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting. (M. D. Gershon, et al., The Peripheral Actions of 5-Hydroxytryptamine, 246 (1989); P. R. Saxena, et al., Journal of Cardiovascular Pharmacology, 15: Supplement 7 (1990).)

The major classes of serotonin receptors (5-HT$_{1-7}$) contain fourteen to eighteen separate receptors that have been formally classified. See Glennon, et al., Neuroscience and Behavioral Reviews, 1990, 14, 35; and D. Hoyer, et al. Pharmacol. Rev. 1994, 46, 157–203. Recently discovered information regarding subtype identity, distribution, structure, and function suggests that it is possible to identify novel, subtype specific agents, having improved therapeutic profiles (e.g. fewer side effects).

For example, the 5-HT$_2$ family of receptors is comprised of 5-HT$_{2A}$, 5-HT$_{2B}$, and 5-HT$_{2C}$ subtypes, which have been grouped together on the basis of primary structure, secondary messenger system, and operational profile. All three subtypes are G-protein coupled, activate phospholipase C as a principal transduction mechanism, and contain a seven-transmembrane domain structure. There are distinct differences in the distribution of the three 5-HT$_2$ subtypes. The 5-HT$_{2B}$ and 5-HT$_{2A}$ receptors are widely distributed in the periphery, while the 5-HT$_{2C}$ receptor has been found only in the central nervous system, being highly expressed in many regions of the human brain. See G. Baxter, et al. Trends in Pharmacol. Sci. 1995, 16, 105–110.

Subtype 5-HT$_{2A}$ has been associated with effects including vasoconstriction, platelet aggregation, and bronchoconstriction, while subtype 5-HT$_{2C}$ has been associated with diseases that include depression, anxiety, obsessive compulsive disorder, panic disorders, phobias, psychiatric syndromes, and obesity. Very little is known about the pharmacological role of the 5-HT$_{2B}$ receptor. See F. Jenck, et al., Exp. Opin. Invest. Drugs, 1998, 7, 1587–1599; M. Bos, et al., J. Med. Chem., 1997, 40, 2762–2769; J. R. Martin, et al., The Journal of Pharmacology and Experimental Therapeutics, 1998, 286, 913–924; S. M. Bromidge, et al., J. Med. Chem., 1998, 41, 1598–1612; G. A. Kennett, Drugs, 1998, 1, 4, 456–470; and A. Dekeyne, et al., Neuropharmacology, 1999, 38, 415–423.

There is currently a need for pharmaceutical agents that are useful to treat diseases and conditions that are associated with 5-HT receptors.

SUMMARY OF THE INVENTION

In accordance with the present invention, novel compounds which demonstrate useful biological activity, and particularly activity as 5-HT receptor ligands, are provided. Thus, the present invention provides a compound of Formula (I):

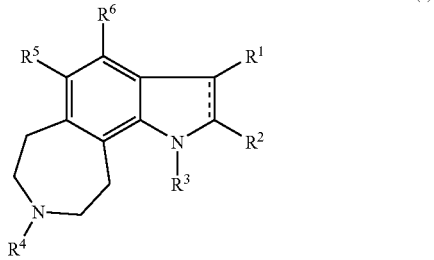

wherein the bond represented by --- is absent or present;

R$^1$ and R$^2$ are independently hydrogen, halo, C$_{1-8}$alkyl, C$_{3-8}$cycloalkyl, hydroxy, cyano, nitro, trifluoromethyl, trifluoromethoxy, C$_{1-8}$alkoxy, C$_{1-8}$alkoxycarbonyl, C$_{1-8}$alkanoyloxy, R$^7$C(=O)—, R$^8$R$^7$NC(=O)—, R$^8$R$^7$N—, aryl, arylC$_{1-8}$alkylene-, heteroaryl, heteroarylC$_{1-8}$alkylene-, Het or HetC$_{1-8}$alkylene-; or R$^1$ and R$^2$ together are a 3-, 4-, 5-, 6-, 7-, or 8-membered saturated or partially unsaturated chain comprising one or more carbon atoms and optionally comprising one or two oxy (—O—), thio (—S—), sulfinyl (—SO—), sulfonyl (S(O)$_2$—), or —NR$^{10}$— in the chain;

R$^3$ is hydrogen, C$_{1-8}$alkyl, C$_{3-8}$cycloalkyl, aryl, heteroaryl, Het, R$^7$C(=O)—, R$^7$OC(=O)—, R$^7$SO$_2$—, R$^8$R$^7$NC(=O)—, R$^7$C(=S)—, R$^7$SC(=O)—, R$^8$R$^7$NC(=S)—, R$^7$SO$_2$—, R$^8$R$^7$NSO$_2$—, R$^7$S(=O)—, R$^8$R$^7$NS(=O)—, R$^a$C$_{1-8}$alkylene- or R$^a$C$_{1-8}$alkyleneC(=O)—;

R$^a$ is aryl, Het, heteroaryl, R$^7$CO$_2$—, R$^7$C(=O)—, R$^7$OC(=O)—, R$^7$O—, R$^7$OC$_{1-8}$alkyleneO—, R$^7$S—, R$^7$C(=S)—, R$^7$S(=O)—, R$^7$SC(=O)—, R$^8$C(=O)N(R$^7$)—, R$^8$C(=S)N(R$^7$)—, R$^8$R$^7$N—, R$^8$R$^7$NC(=O)—, R$^8$R$^7$NC(=S)—, R$^8$R$^7$NS(=O)—, R$^8$R$^7$NSO$_2$—, R$^8$S(=O)N(R$^7$)—, or R$^8$SO$_2$N(R$^7$)—;

R$^4$ is hydrogen, C$_{1-8}$alkyl, C$_{3-8}$cycloalkyl, aryl, heteroaryl, or Het;

$R^5$ and $R^6$ are independently hydrogen, halo, $C_{1-8}$alkyl, $C_{3-8}$cycloalkyl, hydroxy, cyano, nitro, trifluoromethyl, trifluoromethoxy, $C_{1-8}$alkoxy, $C_{1-8}$alkoxycarbonyl, $C_{1-8}$alkanoyloxy, $R^7C(=O)-$, $R^8R^7NC(=O)-$, $R^8R^7N-$, aryl, aryl$C_{1-8}$alkylene-, heteroaryl, heteroaryl$C_{1-8}$alkylene-, Het or Het$C_{1-8}$alkylene-;

$R^7$ and $R^8$ are independently hydrogen, $C_{1-8}$alkyl, $C_{3-8}$cycloalkyl, Het, aryl, heteroaryl, aryl$C_{1-8}$alkylene- or heteroaryl$C_{1-8}$alkylene-;

wherein any aryl, heteroaryl or Het of $R^1$, $R^2$, $R^3$, $R^4$, $R^5$, $R^6$, $R^7$ and $R^8$ is optionally substituted with one or more halo, $C_{1-8}$alkyl, phenyl, cyano, nitro, trifluoromethyl, trifluoromethoxy, $-OR^{10}$, $-SR^{10}$, $-SO_2R^{10}$, $-SO_2NR^{10}R^{11}$, $-NR^{10}R^{11}$, $-C(=O)NR^{10}R^{11}$, $-NR^{10}C(=O)R^{11}$, $-NR^{10}C(=O)NR^{11}R^{12}$, $-CO_2R^{10}$, $-C(=O)R^{10}$, $-OC(=O)R^{10}$, tetrazole, triazole, amidine, guanidine, thioguanidine or cyanoguanidine;

wherein any $C_{1-8}$alkyl, $C_{3-8}$cycloalkyl, $C_{1-8}$alkoxy, $C_{1-8}$alkanoyl, $C_{1-8}$alkoxycarbonyl, or $C_{1-8}$alkanoyloxy of $R^1$, $R^2$, $R^5$, $R^6$, $R^7$, and $R^8$ is optionally substituted with aryloxy, hydroxy, nitro, halo, cyano, $C_{1-8}$alkoxy, $C_{1-8}$alkanoyl, $C_{1-8}$alkoxycarbonyl, $C_{1-8}$alkanoyloxy, $R^{10}S(O)_m-$, $R^{11}R^{10}NS(O)_m-$, $R^{11}R^{10}N-$, or $R^{11}R^{10}NC(=O)-$;

wherein $R^{10}$, $R^{11}$, and $R^{12}$ are independently hydrogen, $C_{1-8}$alkyl, $C_{3-8}$cycloalkyl, aryl, heteroaryl, aryl$C_{1-8}$alkylene- or heteroaryl$C_{1-8}$alkylene;

wherein any $C_{1-8}$alkyl, $C_{1-8}$alkylene, $C_{1-8}$alkoxy, $C_{1-8}$alkanoyl, $C_{1-8}$alkoxycarbonyl, $C_{1-8}$alkanoyloxy or $C_{3-8}$cycloalkyl of $R^1$, $R^2$, $R^3$, $R^4$, $R^5$, $R^6$, $R^7$, $R^8$, $R^{10}$, $R^{11}$, and $R^{12}$ is optionally partially unsaturated;

m is 0, 1, or 2;

or a pharmaceutically acceptable salt thereof.

A specific compound of the invention is of Formula (II):

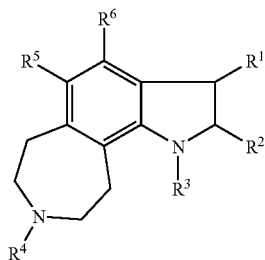

(II)

wherein $R^1$, $R^2$, $R^3$, $R^4$, $R^5$, and $R^6$ are as defined herein.

A specific compound of the invention is of Formula (III):

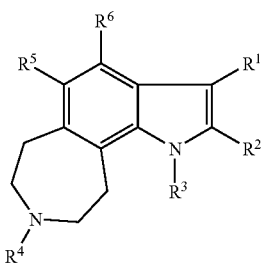

(III)

wherein $R^1$, $R^2$, $R^3$, $R^4$, $R^5$, and $R^6$ are as defined herein.

In another aspect, the present invention also provides:

a pharmaceutical composition comprising a compound of Formula (I), or a pharmaceutically acceptable salt thereof, and a pharmaceutically acceptable excipient (the composition preferably comprises a therapeutically effective amount of the compound or salt thereof), a method for treating a disease or condition in a mammal (e.g. a human) in need thereof, wherein a 5-HT receptor is implicated and modulation of a 5-HT function is desired comprising administering a therapeutically effective amount of a compound of Formula (I), or a pharmaceutically acceptable salt thereof to the mammal, a method for treating or preventing a disease or disorder of the central nervous system in a mammal in need thereof comprising administering a therapeutically effective amount of a compound of Formula (I), or a pharmaceutically acceptable salt thereof to the mammal in need thereof, a compound of Formula (I) or a pharmaceutically acceptable salt thereof for use in medical diagnosis or therapy (e.g. the treatment or prevention of 5-HT related disease such as anxiety, obesity, depression, or a stress-related disease), the use of a compound of Formula (I), or a pharmaceutically acceptable salt thereof to prepare a medicament useful for treating or preventing a disease or disorder of the central nervous system in a mammal, and a method for modulating 5-HT receptor function, comprising administering an effective modulatory amount of a compound of Formula (I), or a pharmaceutically acceptable salt thereof.

The invention also provides novel intermediates (Formula IV) and processes disclosed herein that are useful for preparing compounds of Formula (I):

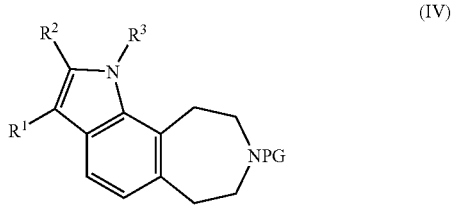

(IV)

wherein $R^1$, $R^2$, $R^3$, and PG are as defined herein.

DETAILED DESCRIPTION OF THE INVENTION

The compounds of the invention are useful for treating or preventing diseases or disorders of the central nervous system. Specific diseases or disorders of the central nervous system for which a compound of Formula (I) may have activity include, but are not limited to: obesity, depression, schizophrenia, schizophreniform disorder, schizoaffective disorder, delusional disorder, a stress-related disease (e.g. general anxiety disorder), panic disorder, a phobia, obsessive compulsive disorder, post-traumatic-stress syndrome, immune system depression, a stress-induced problem with the urinary, gastrointestinal or cardiovascular system (e.g., stress incontinence), neurodegenerative disorders, autism, chemotherapy-induced vomiting, hypertension, migraine, headaches, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, generalized anxiety disorder, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a sleep disorder, a specific development disorder, agitation disorder, selective serotonin reuptake inhibition (SSRI) "poop out" syndrome or a Tic disorder (e.g., Tourette's syndrome).

The present invention provides a compound of Formula (I):

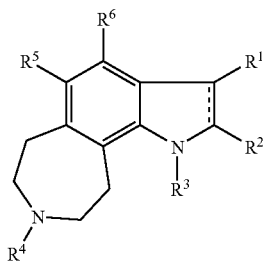

(I)

wherein the bond represented by --- is absent or present;

$R^1$ and $R^2$ are independently hydrogen, halo, $C_{1-8}$alkyl, $C_{3-8}$-cycloalkyl, hydroxy, cyano, nitro, trifluoromethyl, trifluoromethoxy, $C_{1-8}$alkoxy, $C_{1-8}$alkoxycarbonyl, $C_{1-8}$alkanoyloxy, $R^7C(=O)-$, $R^8R^7NC(=O)-$, $R^8R^7N-$, aryl, aryl$C_{1-8}$alkylene-, heteroaryl, heteroaryl$C_{1-8}$alkylene-, Het or Het$C_{1-8}$alkylene-; or $R^1$ and $R^2$ together are a 3-, 4-, 5-, 6-, 7-, or 8-membered saturated or partially unsaturated chain comprising one or more carbon atoms and optionally comprising one or two oxy (—O—), thio (—S—), sulfinyl (—SO—), sulfonyl ($S(O)_2$—), or —$NR^{10}$— in the chain;

$R^3$ is hydrogen, $C_{1-8}$alkyl, $C_{3-8}$cycloalkyl, aryl, heteroaryl, Het, $R^7C(=O)-$, $R^7OC(=O)-$, $R^7SO_2-$, $R^8R^7NC(=O)-$, $R^7C(=S)-$, $R^7SC(=O)-$, $R^8R^7NC(=S)-$, $R^7SO_2-$, $R^8R^7NSO_2-$, $R^7S(=O)-$, $R^8R^7NS(=O)-$, $R^aC_{1-8}$alkylene- or $R^aC_{1-8}$alkyleneC(=O)—;

$R^a$ is aryl, Het, heteroaryl, $R^7CO_2-$, $R^7C(=O)-$, $R^7OC(=O)-$, $R^7O-$, $R^7OC_{1-8}$alkyleneO—, $R^7S-$, $R^7C(=S)-$, $R^7S(=O)-$, $R^7SC(=O)-$, $R^8C(=O)N(R^7)-$, $R^8C(=S)N(R^7)-$, $R^8R^7N-$, $R^8R^7NC(=O)-$, $R^8R^7NC(=S)-$, $R^8R^7NS(=O)-$, $R^8R^7NSO_2-$, $R^8S(=O)N(R^7)-$, or $R^8SO_2N(R^7)-$;

$R^4$ is hydrogen, $C_{1-8}$alkyl, $C_{3-8}$cycloalkyl, aryl, heteroaryl, or Het;

$R^5$ and $R^6$ are independently hydrogen, halo, $C_{1-8}$alkyl, $C_{3-8}$cycloalkyl, hydroxy, cyano, nitro, trifluoromethyl, trifluoromethoxy, $C_{1-8}$alkoxy, $C_{1-8}$alkoxycarbonyl, $C_{1-8}$alkanoyloxy, $R^7C(=O)-$, $R^8R^7NC(=O)-$, $R^8R^7N-$, aryl, aryl$C_{1-8}$alkylene-, heteroaryl, heteroaryl$C_{1-8}$alkylene-, Het or Het$C_{1-8}$alkylene-;

$R^7$ and $R^8$ are independently hydrogen, $C_{1-8}$alkyl, $C_{3-8}$cycloalkyl, Het, aryl, heteroaryl, aryl$C_{1-8}$alkylene- or heteroaryl$C_{1-8}$alkylene-;

wherein any aryl, heteroaryl or Het of $R^1$, $R^2$, $R^3$, $R^4$, $R^5$, $R^6$, $R^7$ and $R^8$ is optionally substituted with one or more halo, $C_{1-8}$alkyl, phenyl, cyano, nitro, trifluoromethyl, trifluoromethoxy, —$OR^{10}$, —$SR^{10}$, —$SO_2R^{10}$, —$SO_2NR^{10}R^{11}$, —$NR^{10}R^{11}$, —$C(=O)NR^{10}R^{11}$, —$NR^{10}C(=O)R^{11}$, —$NR^{10}C(=O)NR^{11}R^{12}$, —$CO_2R^{10}$, —$C(=O)R^{10}$, —$OC(=O)R^{10}$, tetrazole, triazole, amidine, guanidine, thioguanidine or cyanoguanidine;

wherein any $C_{1-8}$alkyl, $C_{3-8}$cycloalkyl, $C_{1-8}$alkoxy, $C_{1-8}$alkanoyl, $C_{1-8}$alkoxycarbonyl, or $C_{1-8}$alkanoyloxy of $R^1$, $R^2$, $R^5$, $R^6$, $R^7$, and $R^8$ is optionally substituted with aryloxy, hydroxy, nitro, halo, cyano, $C_{1-8}$alkoxy, $C_{1-8}$alkanoyl, $C_{1-8}$alkoxycarbonyl, $C_{1-8}$alkanoyloxy, $R^{10}S(O)_m-$, $R^{11}R^{10}NS(O)_m-$, $R^{11}R^{10}N-$, or $R^{11}R^{10}NC(=O)-$;

wherein $R^{10}$, $R^{11}$, and $R^{12}$ are independently hydrogen, $C_{1-8}$alkyl, $C_{3-8}$cycloalkyl, aryl, heteroaryl, aryl$C_{1-8}$alkylene- or heteroaryl$C_{1-8}$alkylene;

wherein any $C_{1-8}$alkyl, $C_{1-8}$alkylene, $C_{1-8}$alkoxy, $C_{1-8}$alkanoyl, $C_{1-8}$alkoxycarbonyl, $C_{1-8}$alkanoyloxy or $C_{3-8}$cycloalkyl of $R^1$, $R^2$, $R^3$, $R^4$, $R^5$, $R^6$, $R^7$, $R^8$, $R^{10}$, $R^{11}$, and $R^{12}$ is optionally partially unsaturated;

m is 0, 1, or 2;

or a pharmaceutically acceptable salt thereof.

A specific compound of the invention is of Formula (II):

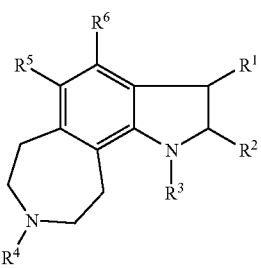

(II)

wherein $R^1$, $R^2$, $R^3$, $R^4$, $R^5$, and $R^6$ are as defined herein.

A specific compound of the invention is of Formula (III):

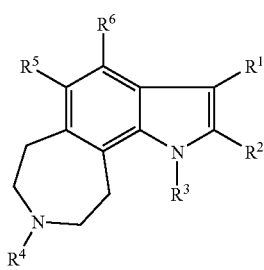

(III)

wherein $R^1$, $R^2$, $R^3$, $R^4$, $R^5$, and $R^6$ are as defined herein.

The invention also provides novel intermediates (Formula IV) and processes disclosed herein that are useful for preparing compounds of Formula (I):

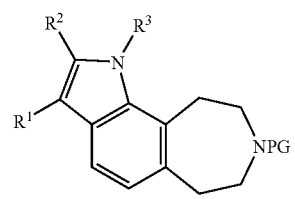

(IV)

wherein $R^1$, $R^2$, $R^3$, and PG are as defined herein.

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. When alkyl or alkylene can be partially unsaturated, the alkyl chain may comprise one or more (e.g. 1, 2, 3, or 4) double or triple bonds in the chain.

Aryl denotes a phenyl radical or an ortho-fused bicyclic carbocyclic radical having about nine to ten ring atoms in which at least one ring is aromatic. Heteroaryl denotes a radical of a monocyclic aromatic ring containing five or six ring atoms consisting of carbon and 1, 2, 3, or 4 heteroatoms each independently selected from the group consisting of non-peroxide oxygen, sulfur, and N(X) wherein X is absent or is H, O, $C_{1-8}$alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term "Het" generally represents a non-aromatic heterocyclic group, which can be saturated or partially unsaturated, containing at least one heteroatom independently selected from the group consisting of oxygen, nitrogen, and sulfur. Specific, "Het" groups include monocyclic, bicyclic, or tricyclic groups containing one or more heteroatoms independently selected from the group consisting of oxygen, nitrogen, and sulfur. A "Het" group also can include one or more oxo groups (=O) attached to a ring atom where valency allows. Nonlimiting examples of Het groups include 1,3-dioxolanyl, 1,4-dioxanyl, 1,4-dithianyl, 2H-pyranyl, 2-pyrazolinyl, 4H-pyranyl, chromanyl, imidazolidinyl, imidazolinyl, indolinyl, isochromanyl, isoindolinyl, morpholinyl, piperazinyl, piperidinyl, piperidyl, pyrazolidinyl, pyrazolidinyl, pyrazolinyl, pyrrolidinyl, pyrrolinyl, quinuclidinyl, thiomorpholinyl, and the like.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, tautomeric, or stereoisomeric form, or mixture thereof, of a compound of the invention, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine 5-HT activity using the standard tests which are well known in the art.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-8}$alkyl refers to alkyl of one to eight carbon atoms, inclusive.

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Specific and preferred values listed below for radicals, substituents, and ranges are for illustration only; they do not exclude other defined values or other values within defined ranges for the radicals and substituents.

Specifically, $C_{1-8}$alkyl can be methyl, ethyl, propyl, isopropyl, butyl, iso-butyl, sec-butyl, pentyl, 3-pentyl, hexyl, or heptyl; $C_{1-8}$alkoxy can be methoxy, ethoxy, propoxy, isopropoxy, butoxy, iso-butoxy, sec-butoxy, pentoxy, 3-pentoxy, hexyloxy, 1-methylhexyloxy, or heptyloxy; $C_{1-8}$alkanoyl can be acetyl, propanoyl, butanoyl, pentanoyl, 4-methylpentanoyl, hexanoyl, or heptanoyl; $C_{1-8}$alkoxycarbonyl can be methoxycarbonyl, ethoxycarbonyl, propoxycarbonyl, isopropoxycarbonyl, butoxycarbonyl, pentoxycarbonyl, hexyloxycarbonyl, or heptyloxycarbonyl; $C_{1-8}$alkanoyloxy can be acetoxy, propanoyloxy, butanoyloxy, isobutanoyloxy, pentanoyloxy, hexanoyloxy, or heptanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific value for $R^1$ is hydrogen, halo, $C_{1-8}$alkyl, $C_{3-8}$cycloalkyl, cyano, nitro, trifluoromethyl, trifluoromethoxy, $C_{1-8}$alkoxy, aryl or aryl$C_{1-8}$alkylene-.

Another specific value for $R^1$ is hydrogen.
Another specific value for $R^1$ is aryl or substituted aryl.
Another specific value for $R^1$ is phenyl.

A specific value for $R^2$ is hydrogen, halo, $C_{1-8}$alkyl, $C_{3-8}$Cycloalkyl, cyano, nitro, trifluoromethyl, trifluoromethoxy, $C_{1-8}$alkoxy, aryl or aryl$C_{1-8}$alkylene-.

Another specific value for $R^2$ is hydrogen.
Another specific value for $R^2$ is aryl or substituted aryl.
Another specific value for $R^2$ is phenyl.

A specific value for $R^3$ is hydrogen, $C_{1-8}$alkyl, $C_{3-8}$cycloalkyl, aryl, heteroaryl, Het, $R^7C(=O)-$, $R^7SO_2-$, $R^8R^7NC(=O)-$, $R^7SC(=O)-$, $R^aC_{1-8}$alkylene- or $R^aC_{1-8}$alkyleneC(=O)-.

Another specific value for $R^3$ is hydrogen, $C_{1-8}$alkyl, aryl, $R^8R^7NC(=O)C_{1-8}$alkylene- or $R^7OC_{1-8}$alkylene-.

A specific value for $R^7$ is heteroaryl.
A specific value for $R^7$ is thiazolyl, quinolyl or pyridyl.
Another specific value for $R^7$ is aryl.
A more specific value for $R^7$ is phenyl, naphthyl, or tetralyl (tetrahydronaphthyl).
Another specific value for $R^7$ is aryl substituted with at least one chlorine, bromine, or $C_{1-8}$alkyl.
A more specific value for $R^7$ is aryl substituted with methyl.

A more specific value for $R^4$ is hydrogen, $C_{1-8}$alkyl, aryl or substituted aryl.
Another specific value for $R^4$ is hydrogen, methyl or phenyl.

A value for $R^5$ is halo, hydroxy, cyano, nitro, trifluoromethyl, trifluoromethoxy, $C_{1-8}$alkoxy, $C_{1-8}$alkoxycarbonyl, $C_{1-8}$alkanoyloxy, aryl or substituted aryl.

A specific value for $R^5$ is hydrogen.
Another specific value for $R^5$ is aryl or substituted aryl.
Another specific value for $R^5$ is phenyl.

A specific value for $R^6$ is halo, hydroxy, cyano, nitro, trifluoromethyl, trifluoromethoxy, $C_{1-8}$alkoxy, $C_{1-8}$alkoxycarbonyl, $C_{1-8}$alkanoyloxy, aryl or substituted aryl.

A specific value for $R^6$ is hydrogen.
Another specific value for $R^6$ is aryl or substituted aryl.
Another specific value for $R^6$ is phenyl.

A specific group of compounds are compounds of Formula (I) wherein $R^1$, $R^2$, and $R^3$ are each hydrogen and $R^4$ is $C_{1-8}$alkyl; and pharmaceutically acceptable salts thereof.

Another specific group of compounds are compounds of Formula (I) wherein $R^1$, $R^2$, $R^4$, $R^5$ and $R^6$ are each hydrogen and $R^3$ is $R^aC_{1-8}$alkylene-; and pharmaceutically acceptable salts thereof.

Another specific group of compounds are compounds of Formula (I) wherein $R^1$, $R^2$, $R^5$, and $R^6$ are each hydrogen; $R^3$ is $R^a C_{1-8}$alkylene-; and $R^4$ is $C^{1-8}$alkyl- and pharmaceutically acceptable salts thereof.

Specifically, the invention also provides a method for treating or preventing anxiety, obesity, depression, schizophrenia, a stress-related disease (e.g. general anxiety disorder), panic disorder, a phobia, obsessive compulsive disorder, post-traumatic-stress syndrome, immune system depression, a stress-induced problem with the gastrointestinal or cardiovascular system, or sexual dysfunction in a mammal (e.g. a human) in need thereof comprising administering a therapeutically effective amount of a compound of Formula (I), or a pharmaceutically acceptable salt thereof to the mammal.

Specifically, the invention also provides a method of treating or preventing anxiety, obesity, depression, or a stress-related disease, comprising administering to a mammal (e.g. a human) in need of such treatment, a therapeutically effective amount of a compound of Formula (I) or a pharmaceutically acceptable salt thereof.

Specifically, the invention also provides the use of a compound of Formula (I) or a pharmaceutically acceptable salt thereof to prepare a medicament for treating or preventing anxiety, obesity, depression, schizophrenia, a stress-related disease (e.g. general anxiety disorder), panic disorder, a phobia, obsessive compulsive disorder, post-traumatic-stress syndrome, immune system depression, a stress-induced problem with the gastrointestinal or cardiovascular system, or sexual dysfunction in a mammal (e.g. a human).

Specifically, the invention also provides the use of a compound of Formula (I) or a pharmaceutically acceptable salt thereof to prepare a medicament for treating or preventing anxiety, obesity, depression, or a stress-related disease in a mammal (e.g. a human).

The invention also provides a method for preparing a compound of Formula (I), wherein $R^3$ or $R^4$ is hydrogen comprising deprotecting a corresponding compound of Formula (I), wherein $R^3$ or $R^4$ is a suitable nitrogen protecting group.

Compounds of the invention can generally be prepared using the synthetic schemes illustrated in Schemes 1–4. Starting materials can be prepared by procedures described in these schemes or by procedures that would be well known to one of ordinary skill in organic chemistry. The variables used in the Schemes are as defined below or as in the claims.

Compounds of Formula (I) can be prepared by reactions outlined in Schemes 1 to 4. The intermediates used in the synthesis to prepare compounds of Formula (I) can be prepared as illustrated in Schemes 1 and 2, wherein the protecting group (PG) is —COOMe and -Boc, respectively.

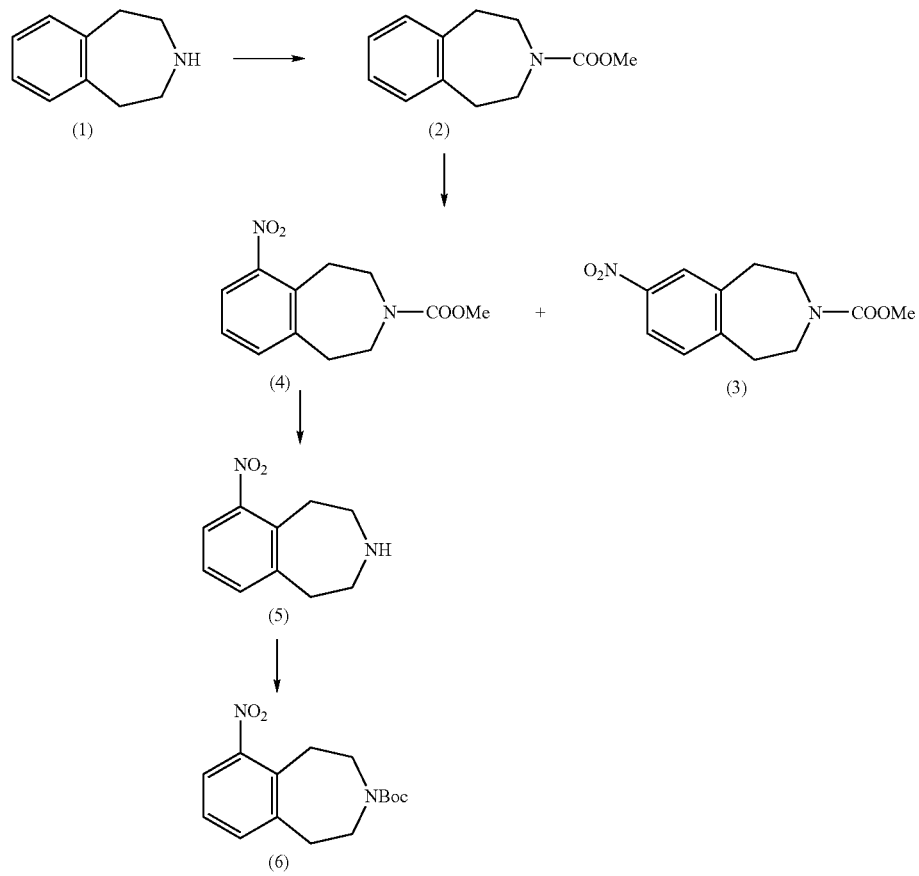

Scheme 1 illustrates the synthesis of intermediates 4 and 6 (PG is COOMe and Boc respectively). Benzoazepine (1) (Pecherer, B. et al., *J. Heterocycl. Chem.*, 2, 609 (1972)) is protected with methylcarbamate and nitrated under the standard nitration conditions, well known to one skilled in the art of organic synthesis, such as, for example, NH$_4$NO$_3$/H$_2$SO$_4$, to provide a mixture of two regio-isomers 3 and 4, which can be separated by chromatography. Treatment of compound 4 with Ba(OH)$_2$ provides intermediate 5, in which the Boc group can be introduced using a standard method (for example, Boc$_2$O/Dioxane).

Lewis acid such as BBr$_3$ to provide hydroxy compound 9, which is converted to the corresponding triflate 10 under the Buchwald/Hartwig conditions (see Yang, B. H. et al., *J. Organomet. Chem.*, 576, 125 (1999) and Hartwig, J. F., *Angew. Chem., Int. Ed. Engl.*, 37, 2046 (1998)). The aniline 11 can be formed after reaction of triflate 10 with benzophe-

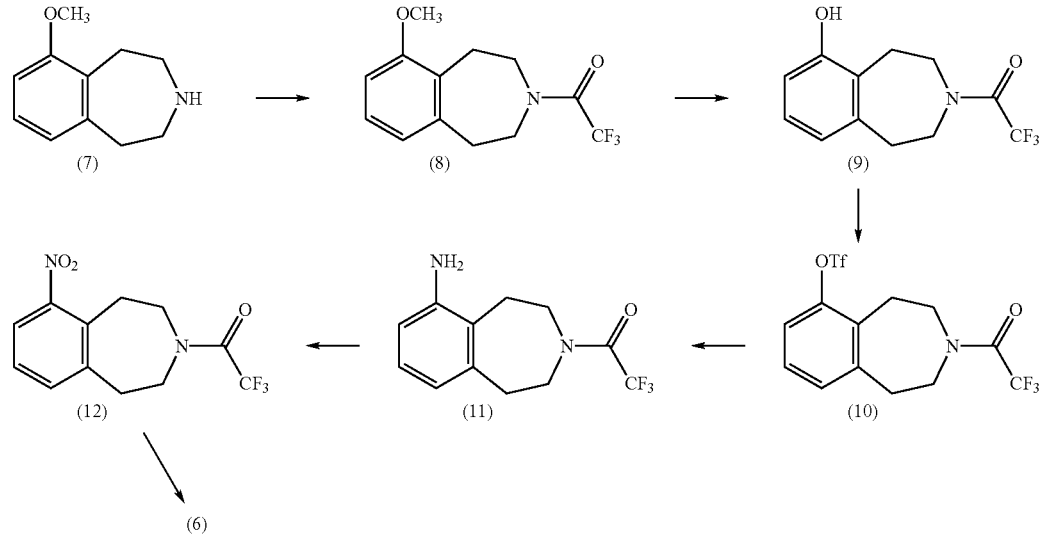

Scheme 2

Scheme 2 illustrates an alternative method for preparation of intermediate 6. The methoxybenzoazepine 7 (Pecherer, B. et al., *J. Heterocycl. Chem.*, 9, 609 (1972)) is protected with a trifluoroacetyl group and subsequent demethylation with a none imine followed by acidic hydrolysis. Aniline 11 is oxidized to provide nitro compound 12, and the protecting group is converted to a Boc group to provide compound 6.

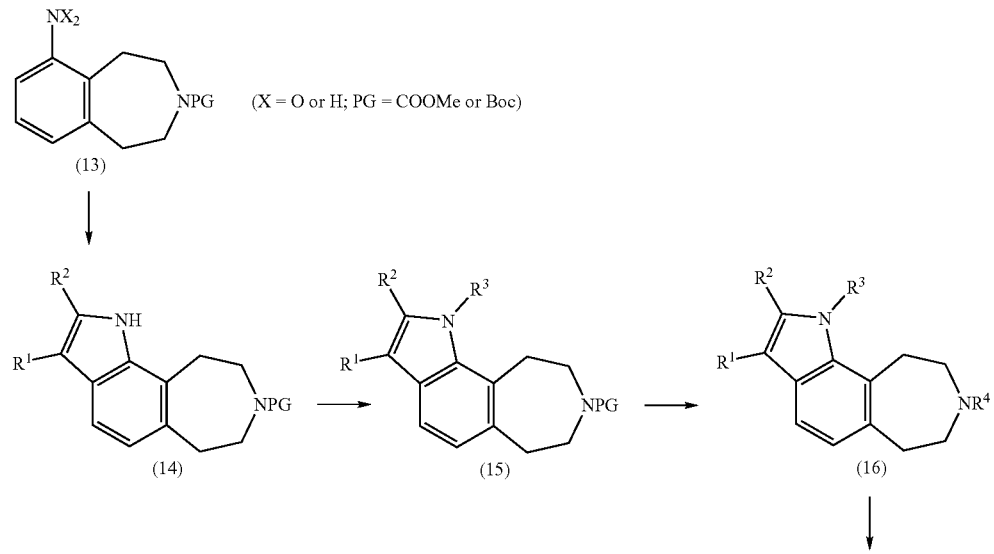

Scheme 3

-continued

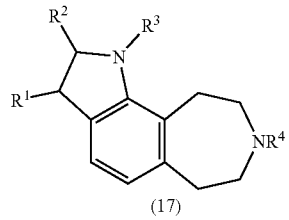

(17)

Compounds of Formula (I) can be prepared by the reactions outlined in Scheme 3 (where X is H or O) by constructing the indole ring (see, *Indoles, Best Synthetic Methods@* Academic Press, 1999, San Diego, Calif.). For example, when X is hydrogen and PG is COOMe, the aniline reacts with chloral hydrate and hydroxylamine to form isatin, which is reduced with LiAlH$_4$ to form the indole ring. Under the same reaction conditions, the carbamate group is reduced to the methyl group. The aniline can also be transformed to the corresponding hydrazine and then subjected to the Fisher indole synthesis conditions to provide indoles. The aniline can also react with a-haloaldehydes or ketones to form the corresponding a-anilino intermediates, which under acidic conditions can lead to the indole formation.

In Scheme 3, compounds where X is oxygen, the nitro compound can be subjected to the Bartoli indole synthesis. (See Bartoli, G. et al., *Tetrahedron Lett.,* 30, 2129 (1989).) The conditions employed, vinylmagnesium chloride/THF, provide indole 14 (R$^1$ and R$^2$ are each hydrogen). In compound 15, when R$^1$ is hydrogen, the electrophilic substitution can lead to the introduction of a variety of electrophiles, for example, the acyl and nitro groups and halogens. The compounds of 15, when R$^1$ or R$^2$ are halogens, can react with a variety of aryl boronic acids using a palladium catalyst such as, for example, Pd(PPh$_3$)$_4$, Pd$_2$(dba)$_3$, Pd(OAc)$_2$, and the like to form the arylated indoles. (See e.g., Miyaura, N. et al., *Chem. Rev.,* 95, 2457 (1995).) To introduce R$^3$ as an aryl (or heteroaryl) group, the reaction is carried out using palladium catalyst such as a palladium dibenzylidine acetone (dba) catalyst (Pd$_2$(dba)$_3$) in the presence of base such as sodium tert-butoxide or K$_3$PO$_4$ with a variety of aryl or heteroaryl halides or aryl or heteroaryl triflates. (See Old, D. W., et al., *Org. Lett.,* 2, 1403 (2000).)

The R$^4$ group can be introduced (15 to 16) by starting with cleavage of the protecting groups (*Protective Groups in Organic Synthesis, 2nd Edition@* Greene and Wuts, John Wiley and Sons, Inc, New York (1991)). Then the secondary amine can be derivatized with an alkyl halide or alkyl mesylate in the presence of a base such as triethylamine or sodium carbonate in solvents such as acetonitrile or dimethyl formamide (DMF) (see, e.g., Glennon, et al., *Med. Chem. Res.,* 197 (1996)) or standard reductive alkylation conditions such as treatment with an aldehyde in the presence of sodium cyanoborohydride under acidic conditions using acids such as trifluoroacetic acid (TFA) to provide the R$^4$-substituted products. (See for example, Lane, C. F., Sodium Cyanoborohydride—A Highly Selective Reducing Agent for Organic Functional Groups@, *Synthesis,* 135 (1975).)

Compound 16 can be reduced with sodium cyanoborohydride in an acidic media such as TFA or acetic acid to give the formation of the indoline compound 17.

Scheme 4

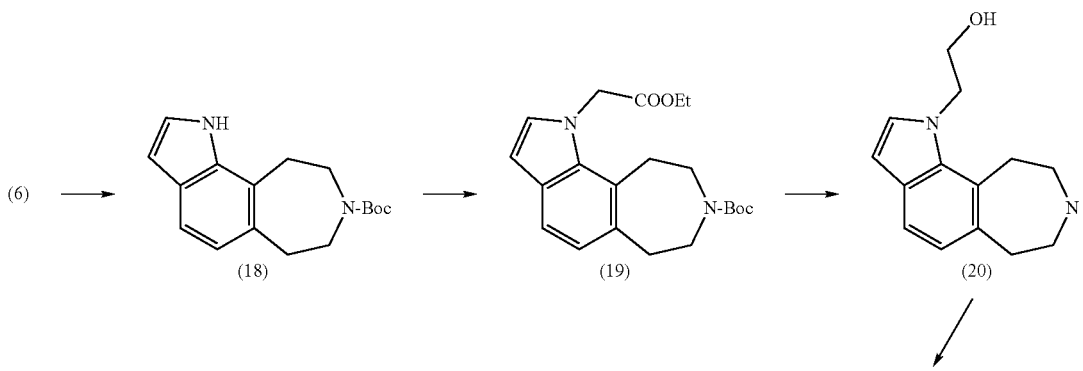

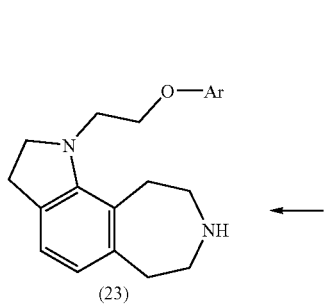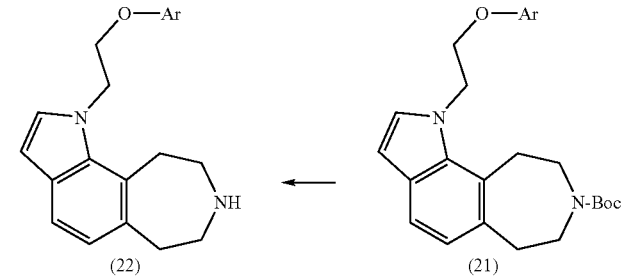

Scheme 4 illustrates the manipulations of the $R^3$ group at the indole nitrogen. The indole nitrogen is alkylated with an alkyl halide or alkyl mesylate in the presence of base such as triethylamine, sodium hydride or sodium (or cesium) carbonate in solvents such as acetonitrile or DMF. (See Glennon, et al., *Med. Chem. Res.*, 197 (1996).) For example, ethyl bromoacetate can be used to form compound 19, which is selectively reduced with LiBH$_4$ to provide alcohol 20. Mitsunobu reaction with a variety of hydroxy aromatics affords the aryl ether compounds 21. Deprotection with an acid such as, for example, HCl, TFA, or β-chlorocatecholborane, generates the desired product, 22. Compound 22 can also be reduced with sodium cyanoborohydride in an acidic media such as TFA or acetic acid to give the formation of the indoline compound 23.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the present invention can conveniently be administered in a pharmaceutical composition containing the compound or salt thereof in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound or salt thereof may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye, and/or flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds or salts thereof may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of Formula (I) can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 10 mg/kg of mammal body weight.

For parenteral administration, the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

The ability of a compound of the invention to act as a 5-HT receptor agonist or antagonist can also be determined using in vitro and in vivo assays that are known in the art. The invention provides compounds of Formula (I) that act as either agonists or as antagonists of one or more 5-HT receptor subtypes. The compounds of the invention are 5-HT ligands, which typically displace >50% of a radiolabeled test ligand from one or more 5-HT receptor subtype at a concentration of 1 μM. The procedures used for testing such displacement are well known and would be readily available to one skilled in the art. For example, see L. W. Fitzgerald, et al., *Mol. Pharmacol*, 2000, 57, 1, 75–81; and D. B. Wainscott, et al., *J. Pharmacol Exp Ther*, 1996, 276, 2, 720–727.

DESCRIPTION OF PREFERRED EMBODIMENTS

Preparation 1

Preparation of tert-butyl 6-nitro-1,2,4,5-tetrahydro-3H-3-benzazepine-3-carboxylate

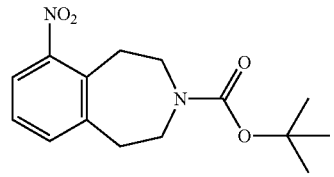

Step a. Methyl 1,2,4,5-tetrahydro-3H-3-benzazepine-3-carboxylate

A flame-dried, 2-L, three-necked flask was charged with 2,3,4,5-tetrahydro-1H-3-benzazepine (95.0 g, 0.645 mol), sodium bicarbonate (108.4 g, 1.29 mol), THF (600 mL), and water (600 mL). The flask was cooled to 0° C. and methyl chloroformate (62.3 mL, 0.81 mol) was added dropwise over 30 min. The bath was removed and the mixture stirred at room temperature for 16 hours. EtOAc was added, the mixture separated, and the aqueous layer was extracted with additional EtOAc. The combined organic layers were concentrated to give 133 g (100%) of the title product as a clear oil which crystallizes at room temperature: $^1$H NMR (300 MHz, CDCl$_3$)δ 7.15–7.13 (m, 4 H), 3.76 (s, 3 H), 3.71–3.53 (m, 4 H), 2.99–2.82 (m, 4 H); MS (ESI+) m/z 206 (M+H)$^+$.

Step b. Methyl 7-nitro-1,2,4,5-tetrahydro-3H-3-benzazepine-3-carboxylate and methyl 6-nitro-1,2,4,5-tetrahydro-3H-3-benzazepine-3-carboxylate (Respectively.)

A 2-L, three-necked flask was charged with methyl 1,2, 4,5-tetrahydro-3H-3-benzazepine-3-carboxylate (132.4 g, 0.645 mol) and sulfuric acid (400 mL). In a separate flask ammonium nitrate (54.2 g, 0.677 mol) was added to an ice-brine bath cooled solution of sulfuric acid (400 mL) at −5° C., and stirred until homogeneous. The ammonium nitrate/sulfuric acid solution was added drop-wise over 1 hour to the solution of 1,2,4,5-tetrahydro-3H-3-benzazepine-3-carboxylate in sulfuric acid at −5° C. After 1.5 hours the solution was poured onto ice (2 L). The aqueous mixture was extracted first with EtOAc and then with CH$_2$Cl$_2$. The organic layers were concentrated and dried over magnesium sulfate to give 59.5 g of a orange oil (37%).

The oil was subjected to preparative HPLC and the isomers separated and purified to give pure samples of the title compounds methyl 6-nitro-1,2,4,5-tetrahydro-3H-3-benzazepine-3-carboxylate (1%) and methyl 7-nitro-1,2,4,5-tetrahydro-3H-3-benzazepine-3-carboxylate (20%). For methyl 7-nitro-1,2,4,5-tetrahydro-3H-3-benzazepine-3-carboxylate: IR (diffuse reflectance) 1693, 1517, 1471, 1440, 1415, 1345, 1318, 1310, 1270, 1243, 1199, 1108, 953, 895, 751 cm$^{-1}$; Anal. Calcd for $C_{12}H_{14}N_2O_4$: C, 57.59; H, 5.64; N, 11.19. Found: C, 57.56; H, 5.79; N, 11.19. For methyl 6-nitro-1,2,4,5-tetrahydro-3H-3-benzazepine-3-carboxylate: $^1$H NMR (300 MHz, CDCl$_3$) δ 7.54 (dd, J=1, 8 Hz, 1 H), 7.35–7.33 (m, 1 H), 7.24 (t, J=8 Hz, 1 H), 3.71 (s, 3 H), 3.70–3.61 (m, 4 H), 3.08–2.96 (m, 4 H); MS (FAB) m/z 251 (MH+); HRMS (FAB) calcd for $C_{12}H_{14}N_2O_4$+H 251.1032. found 251.1040. Anal. Calcd for $C_{12}H_{14}N_2O_4$: C, 57.59; H, 5.64; N, 11.19. Found: C, 57.41; H, 5.69; N, 11.22.

Step c. 6-Nitro-2,3,4,5-tetrahydro-1H-3-benzazepine maleate salt

6-Nitro-1,2,4,5-tetrahydro-3H-3-benzazepine-3-carboxylate (1.05 g, 4.2 mmol) was dissolved in methanol (3.0 mL) and barium hydroxide octahydrate (6.31 g, 0.020 mol) and water (6.0 mL) were added and the mixture was heated at 100° C. for 16 hours. The mixture was filtered and the filtrate concentrated and partitioned between EtOAc and water. The organic layer was concentrated to give 0.80 g of a orange-brown oil. Column chromatography (elution with 1–5% CHCl$_3$/MeOH with methanolic ammonia) afforded 0.62 g (78%) of 6-nitro-2,3,4,5-tetrahydro-1H-3-benzazepine as an orange oil. A portion was converted to the maleate salt to give a white solid: mp 193–195° C.; $^1$H NMR (400 MHz, DMSO-d$_6$) δ 8.88 (br, 2 H), 7.74 (dd, J=1, 8 Hz, 1 H), 7.57 (dd, J=1, 7 Hz, 1 H), 7.44 (t, J=8 Hz, 1 H), 6.03 (s, 2 H), 3.29–3.20 (m, 6 H), 3.16–3.13 (m, 2 H); $^{13}$C NMR (100 MHz, DMSO-d$_6$) δ 167.1, 159.2, 150.4, 142.8, 136.0, 133.4, 132.6, 127.8, 122.2, 44.4, 43.9, 31.6, 25.6; IR (diffuse reflectance) 1630, 1570, 1527, 1498, 1491, 1458, 1393, 1349, 1327, 1005, 983, 866, 746, 731, 714 cm$^{-1}$; MS (EI) m/z 192 (M+); HRMS (FAB) calcd for $C_{10}H_{12}N_2O_2$+H 193.0977. found 193.0980. Anal. Calcd for $C_{10}H_{12}N_2O_2 \cdot C_4H_4O_4$: C, 54.54; H, 5.23; N, 9.09. Found: C, 54.50; H, 5.27; N, 9.08.

Step d. Preparation of tert-butyl 6-nitro-1,2,4,5-tetrahydro-3H-3-benzazepine-3-carboxylate 6-Nitro-2,3,4,5-tetrahydro-1H-3-benzazepine (0.51 g, 2.65 mmol) was dissolved in dioxane (4.0 mL) and di-tert-butyl dicarbonate (0.65 g, 3.0 mmol) was added. Once the initial exothermic reaction was over, the solution was heated to 100° C. for 1 hour. The solution was then concentrated and partitioned between EtOAc and water. The organic layer was concentrated to give 0.85 g of an amber oil. Column chromatography (elution with 10–20% EtOAc/heptane) afforded 0.75 g (97%) of the title compound as a clear oil. Crystallization from EtOAc/hexane provided 0.68 g of white crystals: mp 73–76° C.; $^1$H NMR (400 MHz, CDCl$_3$) δ 7.54 (dd, J=1, 8 Hz, 1 H), 7.34 (d, J=7 Hz, 1 H), 7.24 (t, J=8 Hz, 1 H), 3.66–3.60 (m, 4 H), 3.02–2.99 (m, 4 H), 1.42 (s, 9 H); IR (diffuse reflectance) 1676, 1531, 1468, 1454, 1427, 1366, 1314, 1301, 1267, 1241, 1170, 1108, 948, 807, 739 cm$^{-1}$; MS (EI) m/z 292 (M+); HRMS (FAB) calcd for $C_{15}H_{20}N_2O_4$+H 293.1501. found 293.1498. Anal. Calcd for $C_{15}H_{20}N_2O_4$: C, 61.63; H, 6.89; N, 9.58. Found: C, 61.66; H, 6.95; N, 9.55.

Preparation 2

Alternate preparation of tert-butyl 6-nitro-1,2,4,5-tetrahydro-3H-3-benzazepine-3-carboxylate

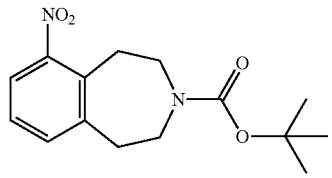

Step a. 6-Methoxy-3-(trifluoroacetyl)-2,3,4,5-tetrahydro-1H-3-benzazepine

6-Methoxy-2,3,4,5-tetrahydro-1H-3-benzazepine (19.11 g, 0.108 mol), CH$_2$Cl$_2$ (100 mL), and triethylamine (16.7 mL, 0.119 mol) were combined and the solution was cooled to 0° C. Trifluoroacetic anhydride (16.2 mL, 0.119 mol) was added slowly via an addition funnel. The solution was then stirred at room temperature for 72 hours. Additional CH$_2$Cl$_2$ was added and the solution was partitioned between CH$_2$Cl$_2$ and water. After extracting with NaHCO$_3$ and washing with H$_2$O, the organic layer was concentrated to give 27.6 g of a brown liquid. Column chromatography (elution with 10–20% EtOAc/heptane) afforded 20.5 g (70%) of the title compound as a brown oil. Crystallization from EtOAc/hexane gave 12.9 g of off-white crystals: mp 75–78° C.; $^1$H NMR (400 MHz, CDCl$_3$) δ 7.16–7.12 (m, 1 H), 6.81 (m, 2 H), 3.81 (s, 3 H), 3.81–3.71 (m, 2 H), 3.70–3.64 (m, 2 H), 3.12–3.07 (m, 2 H), 2.99–2.95 (m, 2 H); IR (diffuse reflectance) 1681, 1468, 1269, 1209, 1189, 1176, 1166, 1151, 1136, 1088, 1004, 950, 780, 754, 739 cm$^{-1}$. MS (EI) m/z 273 (M+); Anal. Calcd for $C_{13}H_{14}F_3N O_2$: C, 57.14; H, 5.16; N, 5.13; F, 20.86. Found: C, 57.23; H, 5.15; N, 5.17.

Step b. 3-(Trifluoroacetyl)-2,3,4,5-tetrahydro-1H-3-benzazepin-6-ol

6-Methoxy-3-(trifluoroacetyl)-2,3,4,5-tetrahydro-1H-3-benzazepine (11.5 g, 42.0 mmol) was dissolved in CH$_2$Cl$_2$ (200 mL) and cooled to 0° C. under nitrogen. Boron tribromide (10.0 mL, 0.105 mol) was added via syringe, and the solution was stirred at room temperature for 16 hours. Saturated ammonium chloride was added slowly with stirring over 2 hours. Additional CH$_2$Cl$_2$ was added and the solution was partitioned between CH$_2$Cl$_2$ and water. The resulting mixture was concentrated and repartitioned between ethyl acetate and H$_2$O. The organic layer was concentrated to give a white solid. Crystallization from EtOAc/hexane gave 9.95 g (91%) of the title compound as a white crystalline solid: mp 183–186° C.; $^1$H NMR (400 MHz, DMSO-d$_6$) δ 6.93 (dt, J=2, 8 Hz, 1 H), 6.71 (dd, J=4, 8 Hz, 1 H), 6.61 (t, J=6 Hz, 1 H), 3.68–3.60 (m, 4 H), 3.00–2.88 (m, 4 H); IR (diffuse reflectance) 3311, 1671, 1466, 1375, 1337, 1313, 1277, 1217, 1199, 1175, 1160, 1147, 949, 785, 739 cm$^{31\ 1}$; MS (EI) m/z 259 (M+); Anal. Calcd for $C_{12}H_{12}F_3N O_2$: C, 55.60; H, 4.67; N, 5.40; F, 21.99. Found: C, 55.24; H, 4.75; N, 5.36.

Step c. 3-(2,2,2-Trifluoroacetyl)-2,3,4,5-tetrahydro-1H-3-benzazepin-6-yl trifluoromethanesulfonate A 500-mL three-necked flask under N$_2$ is charged with 3-(trifluoroacetyl)-2,3,4,5-tetrahydro-1H-3-benzazepin-6-ol (3.97 g, 15.3 mmol), CH$_2$Cl$_2$ (150 mL), and triethylamine (6.4 mL, 45.9 mmol) and the solution was cooled to 0° C. Trifluoromethanesulfonic anhydride (7.7 mL, 45.9 mmol)

was added slowly via syringe over 15 min, and the solution was stirred at room temperature for 16 hours. Saturated ammonium chloride was added slowly with stirring over 2 hours. Additional CH$_2$Cl$_2$ was added and the solution was partitioned between CH$_2$Cl$_2$ and water. After extracting with NaHCO$_3$ and washing with H$_2$O, the organic layer was concentrated to give 8.0 g of a brown oil. Column chromatography (elution with 5–20% EtOAc/heptane) afforded 5.69 g (95%) of the title compound as an oil. An analytical sample was crystallized from EtOAc/hexane to give white crystals: mp 59–61° C.; $^1$H NMR (400 MHz, CDCl$_3$) δ 7.30–7.17 (m, 3 H), 3.82–3.79 (m, 2 H), 3.74–3.71 (m, 2 H), 3.11–3.04 (m, 4 H); IR (diffuse reflectance) 1686, 1466, 1397, 1251, 1208, 1172, 1167, 1150, 1137, 947, 891, 882, 852, 814, 806 cm$^{-1}$; MS (EI) m/z 391 (M+); Anal. Calcd for C$_{13}$H$_{11}$F$_6$N O$_4$S: C, 39.90; H, 2.83; N, 3.58; S, 8.19; F, 29.13. Found: C, 39.89; H, 2.85; N, 3.70.

Step d. 3-(Trifluoroacetyl)-2,3,4,5-tetrahydro-1H-3-benzazepin-6-amine

Under N$_2$, a flame-dried, 500-mL, three-necked flask is charged with palladium acetate (0.60 g, 2.7 mmol), (S)-BINAP (2.5 g, 4.0 mmol), THF (80 mL), 3-(2,2,2-trifluoroacetyl)-2,3,4,5-tetrahydro-1H-3-benzazepin-6-yl trifluoromethanesulfonate (11.7 g, 30.0 mmol), benzophenone imine (6.5 mL, 38.9 mmol) and cesium carbonate (9.8 g, 29.9 mmol). The mixture was heated at 65° C. for 16 hours. The mixture was allowed to cool, ether was added, and the mixture was filtered through celite. The filtrate was concentrated to give 20.8 g of brown oil, combined with a previous lot of the imine intermediate (3.4 g), and subjected to column chromatography (elution with 5–20% EtOAc/heptane). The combined fractions containing the desired compound were collected and concentrated to give 11.8 g of a yellow solid, which was contaminated with benzophenone. The solid was crystallized to give 7.82 g of the imine intermediate as yellow crystals. The mother liquors were subjected to a second column chromatography (elution with 5–20% EtOAc/heptane) to afford an additional 3.37 g of the imine intermediate.

This intermediate (10.27 g, 24.3 mmol) was dissolved in THF (75 mL), HCl (25 mL, 2 N) was added, and the solution was stirred at room temperature for 1 hour. The solution was concentrated and partitioned between HCl (approximately 200 mL 1 N) and hexane:EtOAc (2:1, 400 mL). The aqueous layer was washed with hexane:EtOAc (2:1, 150 mL) to remove the remaining benzophenone impurity. The aqueous layer was then separated and sodium bicarbonate was slowly added with stirring until the pH of the mixture is 7–8. Extraction with CH$_2$Cl$_2$ (2×250 mL) and concentration of the organic layer gives 6.2 g (98%) of the title compound as a clear oil. An analytical sample was crystallized from EtOAc/hexane to give white crystals: mp 85–88° C.; $^1$H NMR (400 MHz, CDCl$_3$) δ 7.00–6.95 (m, 1 H), 6.65–6.58 (m, 2 H), 3.82–3.70 (m, 4 H), 3.61 (br s, 2 H), 2.98–2.95 (m, 2 H), 2.88–2.84 (m, 2 H); (diffuse reflectance)3383, 3253, 1687, 1467, 1382, 1300, 1224, 1212, 1202, 1166, 1126, 778, 756, 730, 662 cm$^{-1}$; MS (EI) m/z 258 (M+); Anal. Calcd for C$_{12}$H$_{13}$F$_3$N$_2$O: C, 55.81; H, 5.07; N, 10.85; F, 22.07. Found: C, 55.87; H, 5.12; N, 10.84.

Step e. 6-Nitro-3-(trifluoroacetyl)-2,3,4,5-tetrahydro-1H-3-benzazepine

Under N$_2$, a flame-dried, 100-mL, three-necked flask is charged with sodium perborate tetrahydrate (5.75 g, 37.4 mmol) and acetic acid (20 mL) and heated to 50–60° C. using an oil bath. A solution of 3-(trifluoroacetyl)-2,3,4,5-tetrahydro-1H-3-benzazepin-6-amine (1.93 g, 7.5 mmol) in acetic acid (20 mL) was slowly added drop-wise over 30 min. The mixture is heated at 55° C. for 1 hour. The mixture was filtered and partitioned between CH$_2$Cl$_2$ and water. The organic layer is washed with water and concentrated to give 2.24 g of an amber oil. Column chromatography (elution with 10–25% EtOAc/heptane) gives 1.52 g (70%) of the title compound as a yellow oil. An analytical sample was crystallized from EtOAc/hexane to give off-white crystals: mp 64–67° C.; $^1$H NMR (400 MHz, CDCl$_3$) δ 7.63 (d, J=8 Hz, 1 H), 7.41–7.29 (m, 2 H), 3.89–3.74 (m, 4 H), 3.15–3.10 (m, 4 H); IR (diffuse reflectance) 1687, 1523, 1466, 1451, 1376, 1368, 1295, 1197, 1186, 1179, 1168, 1147, 950, 818, 752 cm$^{-1}$; MS (EI) m/z 288 (M+); Anal. Calcd for C$_{12}$H$_{11}$F$_3$N$_2$O$_3$: C, 50.01; H, 3.85; N, 9.72; F, 19.77. Found: C, 49.95; H, 3.88; N, 9.68.

Step f. tert-Butyl 6-nitro-1,2,4,5-tetrahydro-3H-3-benzazepine-3-carboxylate

In a round-bottomed flask, 6-nitro-3-(trifluoroacetyl)-2,3,4,5-tetrahydro-1H-3-benzazepine (5.17 g, 17.9 mmol) was dissolved in dioxane (50 mL), and sodium hydroxide (4 N, 13.4 mL, 53.8 mmol) was added. The solution was stirred at room temperature for 2 hours. Di-tert-butyl dicarbonate (7.83 g, 35.9 mmol) was added and the solution was stirred for an additional 16 hours. The solution was concentrated and partitioned between EtOAc and water and the organic layer was concentrated to give 7.1 g of an oil. Column chromatography (elution with 10–30% EtOAc/heptane) gave 5.11 g (98%) of the title compound as an amber oil. The physical properties of the compound obtained were identical to those of the compound obtained from preparation 1.

Preparation 3

Preparation of tert-butyl 1-(2-hydroxyethyl)-6,7,9,10-tetrahydroazepino[4,5-g]indole-8(1H)-carboxylate

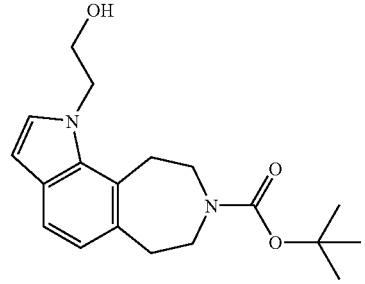

Step a. tert-Butyl 6,7,9,10-tetrahydroazepino[4,5-g]indole-8(1H)-carboxylate

Under N$_2$, a flame-dried, 500-mL, three-necked flask was charged with tert-butyl 6-nitro-1,2,4,5-tetrahydro-3H-3-benzazepine-3-carboxylate (5.49 g, 18.8 mmol) and anhydrous THF (150 mL) and the solution was cooled to −40° C. Vinyl magnesium bromide (100 mL, 94.0 mmol) was added via cannula and the solution was stirred at −20 to −40° C. for 1.5 hours. Saturated ammonium chloride was added and the mixture was allowed to warm to room temperature. The mixture was then partitioned between EtOAc and water. The organic layer was washed with water and the organic layer was concentrated to give 6.72 g of a brown solid. The mixture was then triturated with CH$_2$Cl$_2$ and filtered to give 2.39 g (44%) of the title compound as a beige solid. The remaining filtrate was subjected to column chromatography (elution with 15–25% EtOAc/heptane) to give an additional 0.26 g (5%) of the title compound as an off-white solid. An analytical sample was obtained by triturating with $CH_2Cl_2$ and ether to give white crystals: mp 226–229° C.; $^1$H NMR (400 MHz, DMSO-$d_6$) δ 10.95 (br, 1 H), 7.27–7.25 (m, 2 H), 6.79 (d, J=8 Hz, 1 H), 6.38–6.36 (m, 1 H), 3.55–3.47 (m, 4 H), 3.17–3.08 (m, 2 H), 2.98–2.89 (m, 2 H), 1.40 (s, 9 H); IR (diffuse reflectance) 3289, 2965, 1664, 1475, 1440, 1419, 1365, 1356, 1303, 1226, 1162, 1121, 802, 738, 724 cm$^{-1}$; MS (EI) m/z 286 (M+); HRMS (FAB) calcd for $C_{17}H_{22}N_2O_2$+H 287.1759. found 287.1758. Anal. Calcd for $C_{17}H_{22}N_2O_2$: C, 71.30; H, 7.74; N, 9.78. Found: C, 71.14; H, 7.71; N, 9.63.

Step b. tert-Butyl 1-(2-ethoxy-2-oxoethyl)-6,7,9,10-tetrahydroazepino [4,5-g]-indole-8(1H)-carboxylate Under $N_2$, a flame-dried, 250-mL, three-necked flask was charged with sodium hydride (0.56 g, 13.9 mmol) and anhydrous DMF (20 mL) and cooled to 0° C. A suspension of tert-butyl 6,7,9,10-tetrahydroazepino[4,5-g]indole-8 (1H)-carboxylate (2.66 g, 9.3 mmol) in anhydrous DMF (30 mL) was added and the mixture was stirred at 0° C. for 1 hour and then at room temperature for 30 m. Ethyl bromoacetate (2.06 mL, 18.6 mmol) was added and the mixture was stirred at room temperature for 16 hours. The mixture was partitioned between EtOAc and water and the organic layer was washed with water and the organic layer concentrated to give 4.32 g of a brown oil. Dissolving the oil in $CH_2Cl_2$ and filtration of the resulting precipitate removes unreacted starting material. Column chromatography of the filtrate (elution with 20–50% $Et_2O$/hexane) gave 2.11 g (61%) of the title compound as a white solid: mp 111–115° C.; $^1$H NMR (300 MHz, CDCl$_3$) δ 7.37 (d, J=8 Hz, 1 H), 6.93–6.90 (m, 2 H), 6.48 (d, J=3 Hz, 1 H), 4.98 (s, 2 H), 4.24 (q, J=7 Hz, 2 H), 3.60–3.57 (m, 4 H) 3.17–3.13 (m, 2 H), 3.04–3.00 (m, 2 H), 1.44 (s, 9 H), 1.29 (t, J=7 Hz, 3 H); MS (EI), m/z 372 (M+); HRMS (FAB) calcd for $C_{20}H_{26}N_2O_4$+H 359.1971. found 359.1972. Anal. Calcd for $C_{21}H_{28}N_2O_4$: C, 67.72; H, 7.58; N, 7.52. Found: C, 68.06; H, 7.70; N, 7.73.

Step c. tert-Butyl 1-(2-hydroxyethyl)-6,7,9,10-tetrahydroazepino[4,5-g]indole-8(1H)-carboxylate Under $N_2$, a flame-dried, 100-mL, three-necked flask was charged with lithium borohydride (0.39 g, 17.0 mmol) and anhydrous THF (10 mL) and cooled to −10° C. A solution of tert-butyl 1-(2-ethoxy-2-oxoethyl)-6,7,9,10-tetrahydroazepino[4,5-g]indole-8(1H)-carboxylate (2.11 g, 5.66 mmol) in anhydrous THF (20 mL) was added and the mixture was allowed to warm to room temperature and was stirred for 2 hours. An additional equivalent of lithium borohydride (0.13 mL, 5.66 mmol) was added and the mixture was stirred at room temperature for 16 hours. Water was added slowly and the mixture was partitioned between EtOAc and water. The combined organic layers were concentrated to give 2.09 g of an oil. Column chromatography (elution with 10–30% $Et_2O$/hexane) gave 1.70 g (91%) of the title compound as a clear oil. An analytical sample was crystallized from EtOAc hexane to give a white solid: mp 109–111° C.; $^1$H NMR (400 MHz, CDCl$_3$) δ 7.38 (d, J=8 Hz, 1 H), 7.03 (d, J=3 Hz, 1 H), 6.90 (d, J=8 Hz, 1 H), 6.45 (d, J=3 Hz, 1 H), 4.45 (t, J=5 Hz, 2 H), 3.99–3.88 (m, 2 H), 3.72–3.54 (m, 4 H), 3.39–3.25 (m, 2 H), 3.10–2.99 (m, 2 H), 1.38 (s, 9 H); IR (diffuse reflectance) 3470, 2976, 1666, 1457, 1428, 1369, 1350, 1312, 1267, 1251, 1192, 1178, 1081, 816, 720 cm$^{-1}$; MS (EI) m/z 330 (M+); Anal. Calcd for $C_{19}H_{26}N_2O_3$: C, 69.06; H, 7.93; N, 8.48. Found: C, 68.92; H, 7.94; N, 8.43.

EXAMPLE 1

8-Methyl-1,6,7,8,9,10-hexahydroazepino[4,5-g]indole

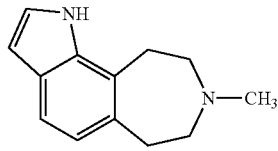

Under $N_2$, a flame-dried, 50-mL, two-necked flask was charged with LiAlH$_4$ (0.10 g, equivalent by weight) and THF (3.0 mL) and cooled to 0° C. A solution of methyl 6,7,9,10-tetrahydroazepino[4,5-g]indole-8(1H)-carboxylate (0.105 g, 0.43 mmol) in THF (2.0 mL) was then added and the mixture was stirred at room temperature for 16 hours. Water (0.1 mL) was added slowly, followed by 15% NaOH (0.1 mL) and then water (0.3 mL). The mixture was stirred for 30 min, celite was added and the mixture was filtered through celite and the filtrate concentrated to give 84 mg (98%) of crude product. Crystallization from EtOAc/hexane affords 27 mg of the title product as a beige solid: mp 150–153° C.; $^1$H NMR (400 MHz, CDCl$_3$) δ 8.09 (br, 1 H), 7.39 (d, J=8 Hz, 1 H), 7.17 (t, J=3 Hz, 1 H), 6.91 (d, J=8 Hz, 6.53 (dd, J=2, 3 Hz, 1 H), 3.10–3.05 (m, 4 H), 2.67–2.62 (m, 4 H), 2.40 (s, 3 H); $^{13}$C NMR (100 MHz, CDCl$_3$) δ 135.5, 135.0, 126.5, 123.8, 123.8, 123.6, 121.9, 118.0, 103.1, 57.7, 56.8, 47.6, 36.2, 29.3; HRMS (FAB) calcd for $C_{13}H_{16}N_2$+H 201.1392. found 201.1390.

The intermediate methyl 6,7,9,10-tetrahydroazepino[4,5-g]indole-8(1H)-carboxylate was prepared as follows.

1(a). Methyl 6,7,9,10-tetrahydroazepino[4,5-g]indole-8(1H)-carboxylate

Under $N_2$, a flame-dried, 100-mL, two-necked flask was charged with 6-nitro-1,2,4,5-tetrahydro-3H-3-benzazepine-3-carboxylate (0.85 g, 3.4 mmol) and THF (20 mL) and cooled to −40° C. Vinyl magnesium bromide (11.2 mL, 11.2 mmol) was added and the solution was stirred for 30 min allowing to warm to −20° C. Ammonium chloride was added and the mixture partitioned between EtOAc and water. The organic layer was concentrated to give 0.88 g of a brown oil. Column chromatography (elution with 10–30% EtOAc/heptane) afforded 0.28 g (34%) of the title compound as a solid. Crystallization from EtOAc/hexane affords 0.192 g of a white solid: mp 169–171° C.; $^1$H NMR (400 MHz, CDCl$_3$) δ 7.41 (d, J=8 Hz, 1 H), 7.19–7.17 (m, 1 H), 6.90 (d, J=8 Hz, 1 H), 6.53–6.52 (m, 1 H), 3.76 (s, 3 H), 3.72–3.63 (m, 4 H), 3.19–3.10 (m, 1 H), 3.00–3.10 (m, 3 H); $^{13}$C NMR (100 MHz, CDCl$_3$) δ 156.6, 135.5, 134.1, 133.6, 126.6, 124.3, 122.7, 118.3, 102.9, 52.7, 47.4, 46.0, 37.3, 30.4; IR (diffuse reflectance) 3313, 1673, 1476, 1446, 1414, 1275, 1260, 1237, 1217, 1115, 947, 805, 764, 745, 731 cm$^{31\ 1}$; MS (EI) m/z 244 (M+); Anal. Calcd for $C_{14}H_{16}N_2O_2$: C, 68.83; H, 6.60; N, 11.47. Found: C, 68.78; H, 6.58; N, 11.43.

EXAMPLE 2

1-(2-Phenoxyethyl)-1,6,7,8,9,10-hexahydroazepino[4,5-g]indole

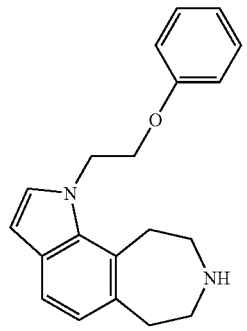

In a flame-dried, 50-mL, two-necked flask, under $N_2$, tert-butyl 1-(2-phenoxyethyl)-6,7,9,10-tetrahydroazepino[4,5-g]indole-8(1H)-carboxylate (0.134 g, 0.33 mmol) was dissolved in $CH_2Cl_2$ (2 mL) and β-chlorocatecholborane (0.105 g, 0.66 mmol) was added and the mixture was allowed to stir at room temperature for 3 hours. Sodium bicarbonate was added and the mixture is stirred for 30 min. and then partitioned between $CH_2Cl_2$ and water. The organic layer was concentrated to dryness in vacuo and the residue was subjected to column chromatography (elution with 5–20% MeOH/$CHCl_3$ with 1% methanolic ammonia) to afford 0.050 g (50%) of a clear oil: $^1$H NMR (400 MHz, $CDCl_3$) δ 7.42 (d, J=8 Hz, 1 H), 7.33–7.29 (m, 2 H), 7.11 (d, J=3 Hz, 1 H), 7.02–6.95 (m, 2 H), 6.91–6.88 (m, 2 H), 6.51 (d, J=3 Hz, 1 H), 4.72 (t, J=6 Hz, 2 H), 4.32 (t, J=6 Hz, 2 H), 3.43–3.40 (m, 2 H), 3.13–3.10 (m, 4 H), 3.06–3.03 (m, 2 H); MS (EI) m/z 306 (M+); HRMS (FAB) calcd for $C_{20}H_{22}N_2O$+H 307.1810. found 307.1812. Anal. Calcd for $C_{20}H_{22}N_2O$: C, 78.40; H, 7.24; N, 9.14.

The intermediate tert-butyl 1-(2-phenoxyethyl)-6,7,9,10-tetrahydroazepino[4,5-g]indole-8(1H)-carboxylate was prepared as follows.

2(a). tert-Butyl 1-(2-phenoxyethyl)-6,7,9,10-tetrahydroazepino[4,5-g]indole-8(1H)-carboxylate Under $N_2$, a flame-dried, 50-mL, three-necked flask was charged with tert-butyl 1-(2-hydroxyethyl)-6,7,9,10-tetrahydroazepino[4,5-g]indole-8(1H)-carboxylate (0.148 g, 0.45 mmol), triphenylphosphine (0.177 g, 3.86 mmol), phenol (0.064 g, 0.675 mmol), and anhydrous THF (3 mL). Di-tert-butyl azodicarboxylate (0.155 g, 0.675 mmol) was added and the mixture was allowed to stir at room temperature for 16 hours. An additional alloquot of triphenylphosphine (0.059 g, 0.225 mmol) and di-tert-butyl azodicarboxylate (0.052 g, 0.225 mmol) was added, and the mixture was allowed to stir at room temperature for an additional 60 hours. The mixture was concentrated, dissolved in $CH_2Cl_2$, and directly subjected to column chromatography (elution with 10–30% EtOAc/heptane) to give 0.135 g (74%) of a clear oil: $^1$H NMR (400 MHz, $CDCl_3$) δ 7.42 (d, J=8 Hz, 1 H), 7.32–7.26 (m, 2 H), 7.13 (d, J=3 Hz, 1 H), 7.02–6.94 (m, 2 H), 6.90–6.87 (m, 2 H), 6.50 (d, J=3 Hz, 1 H), 4.73 (t, J=6 Hz, 2 H), 4.31 (t, J=6 Hz, 2 H), 3.91–3.70 (m, 2 H), 3.70–3.63 (m, 2 H), 3.46–3.36 (m, 2 H), 3.14–3.05 (m, 2 H), 1.47 (s, 9 H).

EXAMPLE 3

1-[2-(2-Fluorophenoxy)ethyl]-1,6,7,8,9,10-hexahydroazepino[4,5-g]indole

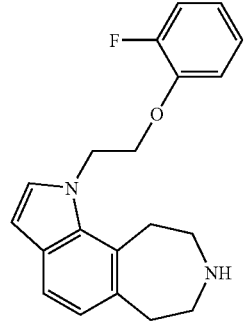

Following procedure of Example 2, the title compound was prepared from tert-butyl 1-[2-(2-fluorophenoxy)ethyl]-6,7,9,10-tetrahydroazepino[4,5-g]indole-8(1H)-carboxylate as an amber oil (34%): $^1$H NMR (400 MHz, $CDCl_3$) δ 7.42 (d, J=8 Hz, 1 H), 7.14–7.08 (m, 3 H), 7.04–6.78 (m, 3 H), 6.51 (d, J=3Hz, 1 H), 4.74 (t, J=6 Hz, 2 H), 4.37 (t, J=7 Hz, 2 H), 3.44–3.41 (m, 2 H), 3.14–3.05 (m, 6 H).

The intermediate tert-butyl 1-[2-(2-fluorophenoxy)ethyl]-6,7,9,10-tetrahydroazepino[4,5-g]indole-8(1H)-carboxylate was prepared as follows.

3(a). tert-Butyl 1-[2-(2-fluorophenoxy)ethyl]-6,7,9,10-tetrahydroazepino-[4,5-g]indole-8(1H)-carboxylate Following the procedure of Example 2(a), using 2-fluorophenol in place of phenol, the title compound was prepared as a white crystalline solid (74%): mp 132–134° C.; $^1$H NMR (400 MHz, $CDCl_3$) δ 7.42 (d, J=8 Hz, 1 H), 7.15–6.86 (m, 6 H), 6.51 (s, 1 H), 4.77 (t, J=6 Hz, 2 H), 4.37 (t, J=6 Hz, 2 H), 3.80–3.70 (m, 2 H), 3.70–3.72 (m, 2 H), 3.46–3.37 (m, 2 H), 3.14–3.05 (m, 2 H), 1.46 (s, 9 H); IR (diffuse reflectance) 1690, 1506, 1456, 1423, 1362, 1318, 1282, 1256, 1249, 1201, 1173, 1108, 814, 748, 728 $cm^{-1}$; MS (EI) m/z 424 (M+); Anal. Calcd for $C_{25}H_{29}FN_2O_3$: C, 70.73; H, 6.89; N, 6.60. Found: C, 70.81; H, 6.97; N, 6.51.

EXAMPLE 4

1-[2-(5,6,7,8-Tetrahydro-1-naphthalenyloxy)ethyl]-1,6,7,8,9,10-hexahydroazepino[4,5-g]indole

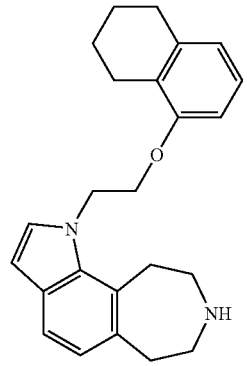

Following procedure of Example 2, the title compound was prepared from tert-butyl 1-[2-(5,6,7,8-tetrahydro-1- naphthalenyloxy)ethyl]-6,7,9,10-tetrahydroazepino[4,5-g]indole-8(1H)-carboxylate as a beige foam (54%): $^1$H NMR (400 MHz, CDCl$_3$) δ 7.42 (d, J=8 Hz, 1 H), 7.14 (d, J=3 Hz, 1 H), 7.05 (t, J=8 Hz, 1 H), 6.95 (d, J=8 Hz, 1 H), 6.73 (d, J=8 Hz, 1 H), 6.57 (d, J=8 Hz, 1 H), 6.50 (d, J=3 Hz, 1 H), 4.72 (t, J=6 Hz, 2 H), 4.28 (t, J=6 Hz, 2 H), 3.52–3.45 (m, 2 H), 3.21–3.00 (m, 6 H), 2.79–2.73 (m, 2 H), 2.64–2.57 (m, 2 H), 1.84–1.73 (m, 4 H); MS (EI) m/z 360 (M+); HRMS (FAB) calcd for C$_{24}$H$_{28}$N$_2$O+H 361.2280. found 361.2284.

The intermediate tert-butyl 1-[2-(5,6,7,8-tetrahydro-1-naphthalenyloxy)ethyl]-6,7,9,10-tetrahydroazepino[4,5-g]indole-8(1H)-carboxylate was prepared as follows.

4(a). tert-Butyl 1-[2-(5,6,7,8-tetrahydro-1-naphthalenyloxy)ethyl]-6,7,9,10-tetrahydroazepino[4,5-g]indole-8(1H)-carboxylate Following the procedure of Example 2(a), using 5,6,7,8-tetrahydro-1-naphthol in place of phenol, the title compound was prepared as a clear oil (30%): $^1$H NMR (400 MHz, CDCl$_3$) δ 7.37 (d, J=8 Hz, 1 H), 7.09 (d, J=3 Hz, 1 H), 6.99 (t, J=8 Hz, 1 H), 6.89 (d, J=8 Hz, 1 H), 6.68 (d, J=8 Hz, 1 H), 6.53 (d, J=8 Hz, 1 H), 6.44 (d, J=3 Hz, 1 H), 4.70 (t, J=6 Hz, 2 H), 4.23 (t, J=5 Hz, 2 H), 3.76–3.65 (m, 2 H), 3.65–3.58 (m, 2 H), 3.39–3.31 (m, 2 H), 3.08–3.00 (m, 2 H), 2.75–2.67 (m, 2 H), 2.59–2.52 (m, 2 H), 1.81–1.79 (m, 4 H), 1.43 (s, 9 H); IR (liq.) 2973, 2930, 2858, 1692, 1585, 1456, 1421, 1366, 1335, 1326, 1316, 1251, 1170, 1097, 765 cm$^{-1}$; MS (EI) m/z 460 (M+); HRMS (FAB) calcd for C$_{29}$H$_{36}$N$_2$O$_3$+H 461.2804. found 461.2814. Anal. Calcd for C$_{29}$H$_{36}$N$_2$O$_3$: C, 75.62; H, 7.88; N, 6.08. Found: C, 75.32; H, 8.17; N, 5.98.

EXAMPLE 5

1-{2-[(5,5-Dimethyl-5,6,7,8-tetrahydro-1-naphthalenyl)oxy]ethyl}-1,6,7,8,9,10-hexahydroazepino[4,5-g]indole

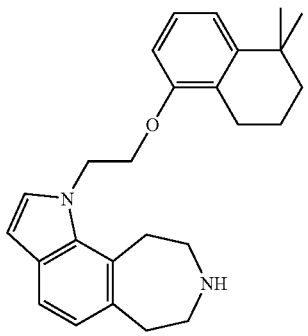

Following the procedure of Example 2, the title compound was prepared from tert-butyl 1-{2-[(5,5-dimethyl-5,6,7,8-tetrahydro-1-naphthalenyl)-oxy]ethyl}-6,7,9,10-tetrahydroazepino[4,5-g]indole-8(1H)-carboxylate as a beige foam (44%): MS (EI) m/z 388 (M+); HRMS (FAB) calcd for C$_{25}$H$_{28}$N$_2$O$_2$+H 389.2229. found 389.2200.

The intermediate tert-butyl 1-{2-[(5,5-dimethyl-5,6,7,8-tetrahydro-1-naphthalenyl)oxy]ethyl}-6,7,9,10-tetrahydroazepino[4,5-g]indole-8(1H)-carboxylate was prepared as follows.

5(a). tert-Butyl 1-{2-[(5,5-dimethyl-5,6,7,8-tetrahydro-1-naphthalenyl)-oxy]ethyl}-6,7,9,10-tetrahydroazepino[4,5-g]indole-8(1H)-carboxylate Following the procedure of Example 2(a), using 5,5-dimethyl-5,6,7,8-tetrahydro-1-naphthol in place of phenol, the title compound was prepared as a clear oil (74%): MS (EI) m/z 488 (M+).

EXAMPLE 6

1-[2-(8-Quinolinyloxy)ethyl]-1,6,7,8,9,10-hexahydroazepino[4,5-g]indole

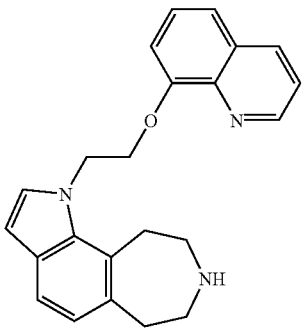

Following the procedure of Example 2, the title compound was prepared from tert-butyl 1-[2-(8-quinolinyloxy)ethyl]-6,7,9,10-tetrahydroazepino[4,5-g]indole-8(1H)-carboxylate as a beige solid (57%): mp 129–132° C.; $^1$H NMR (400 MHz, CDCl$_3$) δ 8.98 (dd, J=2, 4 Hz, 1 H), 8.14 (dd, J=2, 8 Hz, 1 H), 7.46–7.36 (m, 4 H), 7.12 (d, J=3 Hz, 1 H), 6.92 (d, J=8 Hz, 2 H), 6.47 (d, J=3 Hz, 1 H), 4.93 (t, J=7 Hz, 2 H), 4.53 (t, J=7 Hz, 2 H), 3.42–3.39 (m, 2 H), 3.07–2.98 (m, 6 H); $^{13}$C NMR (100 MHz, CDCl$_3$) δ 154.1, 149.6, 140.3, 137.1, 136.0, 134.1, 131.2, 129.6, 129.5, 126.6, 124.7, 122.5, 121.7, 120.6, 118.7, 109.4, 102.0, 68.2, 49.0, 48.1, 47.7, 39.6, 31.8; IR (diffuse reflectance) 2928, 2918, 1501, 1464, 1422, 1379, 1361, 1330, 1316, 1261, 1111, 816, 789, 747, 732 cm$^{-1}$; MS (EI) m/z 357 (M+); HRMS (FAB) calcd for C$_{23}$H$_{23}$N$_3$O+H 358.1919. found 358.1927.

The intermediate tert-butyl 1-[2-(8-quinolinyloxy)ethyl]-6,7,9,10-tetrahydroazepino[4,5-g]indole-8(1H)-carboxylate was prepared as follows.

6(a). tert-Butyl 1-[2-(8-quinolinyloxy)ethyl]-6,7,9,10-tetrahydroazepino[4,5-g]indole-8(1H)-carboxylate Following the procedure of Example 2(a), using 8-hydroxyquinoline in place of phenol, the title compound was prepared as a clear oil (93%): $^1$H NMR (400 MHz, CDCl$_3$) δ 9.00 (s, 1 H), 8.17 (d, J=8 Hz, 1 H), 7.53–7.37 (m, 4 H), 7.17 (br s, 1 H), 6.95 (dd, J=1, 7Hz, 2 H), 6.49 (br s, 1 H), 4.98 (t, J=6 Hz, 2 H), 4.55 (t, J=7 Hz, 2 H), 3.77–3.67 (m, 2 H), 3.67–3.61 (m, 2 H), 3.47–3.38 (m, 2 H), 3.10–3.02 (m, 2 H), 1.41 (s, 9 H); MS (EI) m/z 457 (M+); HRMS (FAB) calcd for C$_{28}$H$_{31}$N$_3$O$_3$+H 458.2443. found 458.2444.

EXAMPLE 7

1-{2-[(5,7-Dichloro-8-quinolinyl)oxy]ethyl}-1,6,7,8,9,10-hexahydroazepino[4,5-g]indole

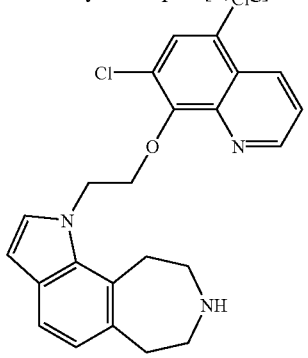

Following the procedure of Example 2, the title compound was prepared from tert-butyl 1-{2-[(5,7-dichloro-8-quinolinyl)oxy]ethyl}-6,7,9,10-tetrahydroazepino[4,5-g]indole-8(1H)-carboxylate as an off-white foam (72%): $^1$H NMR (400 MHz, CDCl$_3$) δ 8.97 (dd, J=2, 4 Hz, 1 H), 8.55 (dd, J=2, 9 Hz, 1 H), 7.66 (s, 1 H), 7.56 (dd, J=4, 9 Hz, 1 H), 7.39 (d, J=8 Hz, 1 H), 7.22 (d, J=3 Hz, 1 H), 6.93 (d, J=8 Hz, 1 H), 6.49 (d, J=3 Hz, 1 H), 4.90 (t, J=7 Hz, 2 H), 4.73 (t, J=7 Hz, 2 H), 3.44–3.40 (m, 2 H), 3.09–3.01 (m, 8 H); MS (EI) m/z 425 (M+); HRMS (FAB) calcd for C$_{23}$H$_{21}$Cl$_2$N$_3$O+H 426.1140. found 426.1136. Anal. Calcd for C$_{23}$H$_{21}$Cl$_2$N$_3$O: C, 64.79; H, 4.96; N, 9.86; Cl, 16.63. Found: C, 64.38; H, 5.17; N, 9.55.

The intermediate tert-butyl 1-{2-[(5,7-dichloro-8-quinolinyl)oxy]ethyl}-6,7,9,10-tetrahydroazepino[4,5-g]indole-8(1H)-carboxylate was prepared as follows.

7(a). tert-Butyl 1-{2-[(5,7-dichloro-8-quinolinyl)oxy]ethyl}-6,7,9,10-tetrahydroazepino[4,5-g]indole-8(1H)-carboxylate Following the procedure of Example 2(a), using 5,7-dichloro-8-hydroxyquinoline in place of phenol, the title compound was prepared as a clear oil (88%): $^1$H NMR (400 MHz, CDCl$_3$) δ 8.96 (s, 1 H), 8.57–8.50 (m, 1 H), 7.63 (s, 1 H), 7.54 (dd, J=6, 11 Hz, 1 H), 7.38 (d, J=11 Hz, 1 H), 7.23 (br, 1 H), 6.96–6.88 (m, 1 H), 6.47 (d, J=1 Hz, 1 H), 4.90 (t, J=9 Hz, 2 H), 4.71 (t, J=8 Hz, 2 H), 3.73–3.57 (m, 4 H), 3.46–3.37 (m, 2 H), 3.08–3.01 (m, 2 H), 1.45 (s, 9 H); MS (EI) m/z 525 (M+); HRMS (FAB) calcd for C$_{28}$H$_{29}$Cl$_2$N$_3$O$_3$+H 526.1664. found 526.1666.

EXAMPLE 8

1-{2-[(5,7-Dibromo-8-quinolinyl)oxy]ethyl}-1,6,7,8,9,10-hexahydroazepino[4,5-g]indole

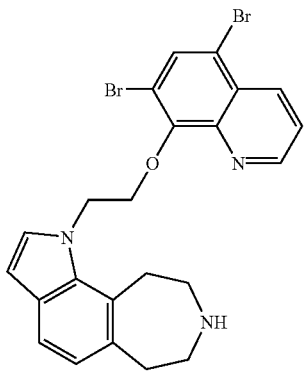

Following the procedure of Example 2, the title compound was prepared from tert-butyl 1-{2-[(5,7-dibromo-8-quinolinyl)oxy]ethyl}-6,7,9,10-tetrahydroazepino[4,5-g]indole-8(1H)-carboxylate as a clear oil (78%): $^1$H NMR (400 MHz, CDCl$_3$) δ 8.93 (d, J=3 Hz, 1 H), 8.51 (d, J=9 Hz, 1 H), 8.00 (s, 1 H), 7.57 (dd, J=4, 9 Hz, 1 H), 7.40 (d, J=8 Hz, 1 H), 7.23 (d, J=3 Hz, 1 H), 6.93 (d, J=8 Hz, 1 H), 6.50 (d, J=3 Hz, 1 H), 4.91 (t, J=7 Hz, 2 H), 4.73 (t, J=7 Hz, 2 H), 3.55–3.47 (m, 2 H), 3.17–3.06 (m, 6 H); HRMS (FAB) calcd for C$_{23}$H$_{21}$Br$_2$N$_3$O+H 514.0131. found, 514.0136.

The intermediate tert-butyl 1-{2-[(5,7-dibromo-8-quinolinyl)oxy]-ethyl}-6,7,9,10-tetrahydroazepino[4,5-g]indole-8(1H)-carboxylate was prepared as follows.

8(a). tert-Butyl 1-{2-[(5,7-dibromo-8-quinolinyl)oxy]ethyl}-6,7,9,10-tetrahydroazepino[4,5-g]indole-8(1H)-carboxylate Following the procedure of Example 2(a), using 5,7-dibromo-8-hydroxyquinoline in place of phenol, the title compound was prepared as a yellow foam (87%): $^1$H NMR (400 MHz, CDCl$_3$) δ 8.92–8.90 (m, 1 H), 8.48 (d, J=8 Hz, 1 H), 7.95 (s, 1 H), 7.54 (dd, J=4, 9 Hz, 1 H), 7.36 (d, J=8 Hz, 1 H), 7.21 (br s, 1 H), 6.89 (d, J=8 Hz, 1 H), 6.44 (d, J=3 Hz, 1 H), 4.90 (t, J=7 Hz, 2 H), 4.69 (t, J=6 Hz, 2 H), 3.72–3.64 (m, 2 H), 3.64–3.57 (m, 2 H), 3.44–3.38 (m, 2 H), 3.07–3.00 (m, 2 H), 1.43 (s, 9 H); IR (diffuse reflectance) 1688, 1482, 1451, 1421, 1390, 1385, 1365, 1345, 1318, 1262, 1248, 1209, 1168, 1106, 809 cm$^{-1}$; MS (EI) m/z 613 (M+); HRMS (FAB) calcd for C$_{28}$H$_{29}$Br$_2$N$_3$O$_3$+H 614.0655. found 614.0646.

Using synthetic procedures similar to those described herein, the following compounds of formula (I) can also be prepared:

EXAMPLE 9

1-(3-Phenoxypropyl)-1,6,7,8,9,10-hexahydroazepino[4,5-g]indole

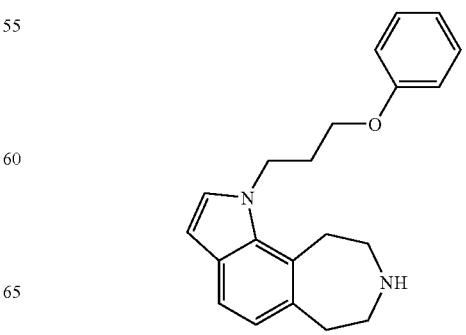

EXAMPLE 10

8-Methyl-1-(3-phenoxypropyl)-1,6,7,8,9,10-hexahydroazepino-[4,5-g]indole

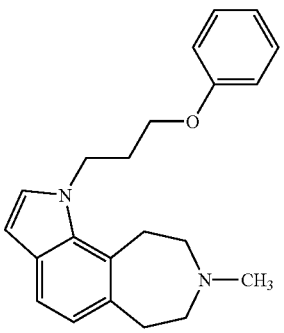

EXAMPLE 11

1-(2-(2,3-dimethylphenylamino)-2-oxoethyl)-1,6,7,8,9,10-hexahydroazepino[4,5-g]indole

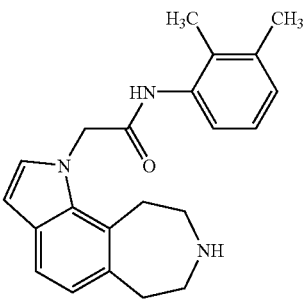

EXAMPLE 12

1-(2-(4-methylthiazol-3-ylamino)-2-oxoethyl)-1,6,7,8,9,10-hexahydroazepino[4,5-g]indole

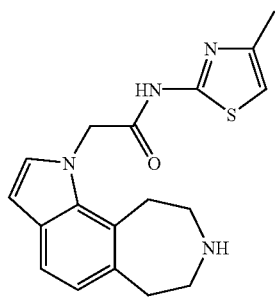

The invention has been described with reference to various specific and preferred embodiments and techniques. However, it should be understood that many variations and modifications may be made while remaining within the spirit and scope of the invention.

What is claimed:

1. A compound of Formula (I):

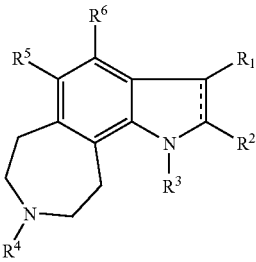

I wherein the bond represented by --- is absent or present;

$R^1$ and $R^2$ are independently hydrogen, halo, $C_{1-8}$alkyl, $C_{3-8}$cycloalkyl, hydroxy, cyano, nitro, trifluoromethyl, trifluoromethoxy, $C_{1-8}$alkoxy, $C_{1-8}$alkoxycarbonyl, $C_{1-8}$alkanoyloxy, $R^7C(=O)-$, $R^8R^7NC(=O)-$, $R^8R^7N-$, aryl, aryl$C_{1-8}$alkylene-, heteroaryl, heteroaryl$C_{1-8}$alkylene-, Het or Het$C_{1-8}$alkylene-; or $R^1$ and $R^2$ together are a 3-, 4-, 5-, 6-, 7-, or 8-membered saturated or partially unsaturated chain comprising one or more carbon atoms and optionally comprising one or two oxy(—O—), thio(—S—), sulfinyl(—SO—), sulfonyl(—S(O)$_2$—), or —NR$^{10}$— in the chain;

$R^3$ is hydrogen, $C_{1-8}$alkyl, $C_{3-8}$cycloalkyl, aryl, heteroaryl, Het, $R^7C(=O)-$, $R^7OC(=O)-$, $R^7SO_2-$, $R^8R^7NC(=O)-$, $R^7C(=S)-$, $R^7SC(=O)-$, $R^8R^7NC(=S)-$, $R^7SO_2-$, $R^8R^7NSO_2-$, $R^7S(=O)-$, $R^8R^7NS(=O)-$, $R^aC_{1-8}$alkylene, or $R^aC_{1-8}$alkyleneC(=O)—;

$R^a$ is aryl, Het, heteroaryl, $R^7CO_2-$, $R^7C(=O)-$, $R^7OC(=O)-$, $R^7O-$, $R^7OC_{1-8}$alkyleneO—, $R^7S-$, $R^7C(=S)-$, $R^7S(=O)-$, $R^7SC(=O)-$, $R^8C(=O)N(R^7)-$, $R^8C(=S)N(R^7)-$, $R^8R^7N-$, $R^8R^7NC(=O)-$, $R^8R^7NC(=S)-$, $R^8R^7NS(=O)-$, $R^8R^7NSO_2-$, $R^8S(=O)N(R^7)-$, or $R^8SO_2N(R^7)-$;

$R^4$ is hydrogen, $C_{1-8}$alkyl, $C_{3-8}$cycloalkyl, aryl, heteroaryl, or Het;

$R^5$ and $R^6$ are independently hydrogen, halo, $C_{1-8}$alkyl, $C_{3-8}$cycloalkyl, hydroxy, cyano, nitro, trifluoromethyl, trifluoromethoxy, $C_{1-8}$alkoxy, $C_{1-8}$alkoxycarbonyl, $C_{1-8}$alkanoyloxy, $R^7C(=O)-$, $R^8R^7NC(=O)-$, $R^8R^7N-$, aryl, aryl$C_{1-8}$alkylene-, heteroaryl, heteroaryl$C_{1-8}$alkylene-, Het or Het$C_{1-8}$alkylene-;

$R^7$ and $R^8$ are independently hydrogen, $C_{1-8}$alkyl, $C_{3-8}$cycloalkyl, Het, aryl, heteroaryl, aryl$C_{1-8}$alkylene- or heteroaryl$C_{1-8}$alkylene;

wherein any aryl, heteroaryl or Het of $R^1$, $R^2$, $R^3$, $R^4$, $R^5$, $R^6$, $R^7$ and $R^8$ is optionally substituted with one or more halo, $C_{1-8}$alkyl, phenyl, cyano, nitro, trifluoromethyl, trifluoromethoxy, —OR$^{10}$, —SR$^{10}$, —SO$_2$R$^{10}$, —SO$_2$NR$^{10}$R$^{11}$, —NR$^{10}$R$^{11}$, —C(=O)NR$^{10}$R$^{11}$, —NR$^{10}$C(=O)R$^{11}$, —NR$^{10}$C(=O)NR$^{11}$R$^{12}$, —CO$_2$R$^{10}$, —C(=O)R$^{10}$, —OC(=O)R$^{10}$, tetrazole, triazole, amidine, guanidine, thioguanidine or cyanoguanidine;

wherein any $C_{1-8}$alkyl, $C_{3-8}$cycloalkyl, $C_{1-8}$alkoxy, $C_{1-8}$alkanoyl, $C_{1-8}$alkoxycarbonyl, or $C_{1-8}$alkanoyloxy of $R^1$, $R^2$, $R^5$, $R^6$, $R^7$, and $R^8$ is optionally substituted with aryloxy, hydroxy, nitro, halo, cyano, $C_{1-8}$alkoxy, $C_{1-8}$alkanoyl, $C_{1-8}$alkoxycarbonyl, $C_{1-8}$alkanoyloxy, $R^{10}S(O)_m-$, $R^{11}R^{10}NS(O)_m-$, $R^{11}R^{10}N-$, or $R^{11}R^{10}NC(=O)-$;

wherein $R^{10}$, $R^{11}$, and $R^{12}$ are independently hydrogen, $C_{1-8}$alkyl, $C_{3-8}$cycloalkyl, aryl, heteroaryl, aryl$C_{1-8}$alkylene-, or heteroaryl$C_{1-8}$alkylene;

wherein any $C_{1-8}$alkyl, $C_{1-8}$alkylene, $C_{1-8}$alkoxy, $C_{1-8}$alkanoyl, $C_{1-8}$alkoxycarbonyl, $C_{1-8}$alkanoyloxy or $C_{3-8}$cycloalkyl that is included in the definition of $R^1$, $R^2$, $R^3$, $R^4$, $R^5$, $R^6$, $R^7$, $R^8$, $R^{10}$, $R^{11}$, or $R^{12}$ is optionally partially unsaturated;

wherein Het is a monocyclic, bicyclic and tricyclic non-aromatic heterocyclic group, which can be saturated or partially unsaturated, containing at least one heteroatom independently selected from the group consisting of oxygen, nitrogen and sulfur;

m is 0, 1, or 2;

or a pharmaceutically acceptable salt thereof.

2. The compound of claim 1, which is a compound of Formula (II):

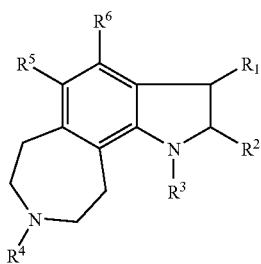

II or a pharmaceutically acceptable salt thereof.

3. The compound of claim 1, which is a compound of Formula (III):

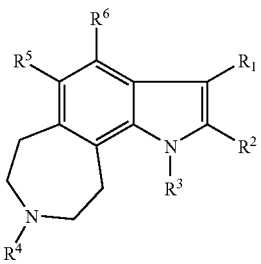

III or a pharmaceutically acceptable salt thereof.

4. The compound of claim 1, wherein $R^1$ and $R^2$ are independently hydrogen, halo, $C_{1-8}$alkyl, $C_{3-8}$cycloalkyl, cyano, nitro, trifluoromethyl, trifluoromethoxy, $C_{1-8}$alkoxy, aryl, or aryl$C_{1-8}$alkylene-.

5. The compound of claim 4, wherein $R^1$ and $R^2$ are independently hydrogen, aryl or substituted aryl.

6. The compound of claim 4, wherein one of $R^1$ and $R^2$ is phenyl.

7. The compound of claim 4, wherein one or both of $R^1$ and $R^2$ is/are hydrogen.

8. The compound of claim 1, wherein $R^3$ is hydrogen, $C_{1-8}$alkyl, $C_{3-8}$cycloalkyl, aryl, heteroaryl, Het, $R^7C(=O)$—, $R^7SO_2$—, $R^8R^7NC(=O)$—, $R^7SC(=O)$—, $R^aC_{1-8}$alkylene-, or $R^aC_{1-8}$alkyleneC(=O)—.

9. The compound of claim 8, wherein $R^3$ is hydrogen, $C_{1-8}$alkyl, aryl, heteroaryl, $R^8R^7NC(=O)C_{1-8}$alkylene-, or $R^7OC_{1-8}$alkylene-.

10. The compound of claim 9, wherein $R^7$ is heteroaryl.

11. The compound of claim 9, wherein $R^7$ is thiazolyl, quinolyl or pyridyl.

12. The compound of claim 11, wherein $R^7$ is substituted with at least one fluorine, chlorine, bromine, or $C_{1-8}$alkyl.

13. The compound of claim 11, wherein $R^7$ is substituted with at least one methyl.

14. The compound of claim 9, wherein $R^3$ is hydrogen or $C_{1-8}$alkyl.

15. The compound of claim 9, wherein $R^7$ is aryl.

16. The compound of claim 9, wherein $R^7$ is phenyl, naphthyl, or tetralyl.

17. The compound of claim 16, wherein $R^7$ is substituted with at least one fluorine, chlorine, bromine, or $C_{1-8}$alkyl.

18. The compound of claim 16, wherein $R^7$ is substituted with at least one methyl.

19. The compound of claim 1, wherein $R^4$ is hydrogen, $C_{1-8}$alkyl, aryl, or substituted aryl.

20. The compound of claim 19, wherein $R^4$ is hydrogen or methyl.

21. The compound of claim 1, wherein $R^5$ and $R^6$ are independently hydrogen, halo, hydroxy, cyano, nitro, trifluoromethyl, trifluoromethoxy, $C_{1-8}$alkoxy, $C_{1-8}$alkoxycarbonyl, $C_{1-8}$alkanoyloxy, aryl, or substituted aryl.

22. The compound of claim 21, wherein $R^5$ and $R^6$ are independently hydrogen, aryl or substituted aryl.

23. The compound of claim 21, wherein $R^5$ and $R^6$ are independently hydrogen or phenyl.

24. The compound of claim 21, wherein $R^5$ and $R^6$ are each hydrogen.

25. The compound of claim 5, wherein $R^1$, $R^2$, and $R^3$ are each hydrogen and $R^4$ is methyl.

26. The compound of claim 1 which is:
8-Methyl-1,6,7,8,9,10-hexyhydroazepino[4,5-g]indole;
1-(2-Phenoxyethyl)-1,6,7,8,9,10-hexyhydroazepino[4,5-g]indole;
1-[2-(2-Fluorophenoxy)ethyl]-1,6,7,8,9,10-hexahydroazepino[4,5-g]indole;
1-[2-(5,6,7,8-Tetrahydro-1-naphthalenyloxy)ethyl]-1,6,7,8,9,10-hexahydroazepino[4,5-g]indole;
1-{2-[(5,5-Dimethyl-5,6,7,8-tetrahydro-1-naphthalenyl)oxy]ethyl}-1,6,7,8,9,10-hexahydroazepino[4,5-g]indole;
1-[2-(8-Quinolinyloxy)ethyl]-1,6,7,8,9,10-hexyhydroazepino[4,5-g]indole;
1-{2-[(5,7-Dichloro-8-quinolinyl)oxy]ethyl}-1,6,7,8,9,10-hexahydroazepino[4,5-g]indole;
1-{2-[(5,7-Dibromo-8-quinolinyl)oxy]ethyl}-1,6,7,8,9,10-hexahydroazepino[4,5-g]indole;
1-(3-Phenoxypropyl)-1,6,7,8,9,10-hexahydroazepino[4,5-g]indole;
8-Methyl-1-(3-phenoxypropyl)-1,6,7,8,9,10-hexahydroazepino-[4,5-g]-indole;
1-(2-(2,3-dimethylphenylamino)-2-oxoethyl)-1,6,7,8,9,10-hexahydroazepino[4,5-g]indole;
1-(2-(4-methylthiaz-3-ylamino)-2-oxoethyl)-1,6,7,8,9,10-hexahydroazepino[4,5-g]indole;
or a pharmaceutically acceptable salt thereof.

27. A pharmaceutical composition comprising a compound of claim 1 and a pharmaceutically acceptable excipient.

28. A method for treating a disease or disorder of the central nervous system in a mammal in need thereof comprising administering a therapeutically effective amount of a compound of claim 1 to the mammal, wherein the disease is selected from the group consisting of anxiety, obesity, depression, obsessive compulsive disorder, phobias and panic disorders.

29. A compound of formula IV:

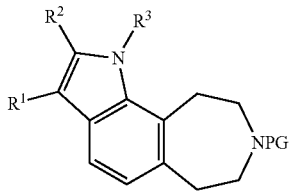

IV wherein $R^1$, $R^2$ and $R^3$ are the same as in claim 1 and PG is COOMe or Boc.

30. The compound according to claim 29, wherein PG is COOMe.

31. The compound according to claim 29, wherein PG is Boc.

32. The compound according to claim 29, wherein $R^3$ is hydrogen or $C_{1-8}$alkyl.

33. The compound according to claim 29, wherein $R^1$ and $R^2$ are independently hydrogen or aryl.

34. The compound according to claim 29, wherein $R^1$, $R^2$, and $R^3$ are hydrogen.

* * * * *